(12) United States Patent
Kelly et al.

(10) Patent No.: US 7,176,322 B2
(45) Date of Patent: Feb. 13, 2007

(54) CALCIUM RECEPTOR MODULATING AGENTS

(75) Inventors: Michael G. Kelly, South San Francisco, CA (US); Shimin Xu, Moorpark, CA (US); Ning Xi, Thousand Oaks, CA (US); Robert Townsend, Barnsley (GB); David Semin, Thousand Oaks, CA (US); Chiara Ghiron, Wootton (GB); Thomas Coulter, Wantage (GB)

(73) Assignee: Amgen Inc., Thousand Oaks, CA (US)

( * ) Notice: Subject to any disclaimer, the term of this patent is extended or adjusted under 35 U.S.C. 154(b) by 260 days.

(21) Appl. No.: 10/444,945

(22) Filed: May 22, 2003

(65) Prior Publication Data

US 2004/0077619 A1    Apr. 22, 2004

Related U.S. Application Data

(60) Provisional application No. 60/383,270, filed on May 23, 2002.

(51) Int. Cl.
*C07D 209/82* (2006.01)
*C07D 209/14* (2006.01)
*C07D 209/04* (2006.01)
*A61K 31/403* (2006.01)
*A61K 31/404* (2006.01)
*A61K 31/4045* (2006.01)

(52) U.S. Cl. ............... 548/469; 548/444; 548/503; 548/509; 514/410; 514/411; 514/412; 514/415

(58) Field of Classification Search ............... 548/469, 548/503, 509, 444; 514/410–412, 415
See application file for complete search history.

(56) References Cited

U.S. PATENT DOCUMENTS

| 5,981,599 | A | 11/1999 | Moe et al. | |
|---|---|---|---|---|
| 6,001,884 | A | 12/1999 | Nemeth et al. | 514/699 |
| 6,011,068 | A | 1/2000 | Nemeth et al. | |
| 6,031,003 | A | 2/2000 | Nemeth et al. | |
| 6,103,737 | A | 8/2000 | Cocuzza et al. | |
| 6,172,091 | B1 | 1/2001 | Cohen et al. | |
| 6,225,316 | B1 | 5/2001 | Bos et al. | |
| 6,335,338 | B1 | 1/2002 | Bhatnagar et al. | |
| 6,403,832 | B1 | 6/2002 | Oikawa et al. | |
| 6,407,111 | B1 | 6/2002 | Bos et al. | |
| 6,436,152 | B1 | 8/2002 | Chassot et al. | |
| 2002/0143212 | A1 | 10/2002 | Oikawa et al. | |

FOREIGN PATENT DOCUMENTS

| EP | 0 039 051 | 11/1981 |
|---|---|---|
| EP | 0 933 354 | 8/1999 |
| WO | WO 93/04373 | 3/1993 |
| WO | WO 94/18959 | 9/1994 |
| WO | WO 95/11221 | 4/1995 |
| WO | WO 96/05818 | 2/1996 |
| WO | WO 96/09818 | 4/1996 |
| WO | WO 96/12697 | 5/1996 |
| WO | WO 96/31475 | 10/1996 |
| WO | WO 97/05252 | 2/1997 |
| WO | WO 97/37967 | 10/1997 |
| WO | WO 97/41090 | 11/1997 |
| WO | WO 98/01417 | 1/1998 |
| WO | WO 98/37061 | 8/1998 |
| WO | WO 98/45255 | 10/1998 |
| WO | WO 99/01439 | 1/1999 |
| WO | WO 00/21910 | 4/2000 |
| WO | WO 01/34562 | 5/2001 |
| WO | WO 01/90069 | 11/2001 |
| WO | WO 01/96307 | 12/2001 |
| WO | WO 01/96365 | 12/2001 |
| WO | WO 02/051805 | 7/2002 |
| WO | WO 02/096424 | * 12/2002 |

OTHER PUBLICATIONS

Nemeth, E. F.; Steffey, L. G.; Jammerland, L. G.; Hung, B. C. P.; Van Wagenen, B. C.; Delmar, E. G.; Balandrin, M. F. Proc. Natl. Acad. Sci. US 1998, 95, 4040-4045.*
Singhal, S.; Johnson, C. A.; Udelsman, R. Orthopedics 2001, 24, 1003-1009.*
Zaidi, M. Bioscience Reports 1990, 10, 493-507.*
Wittig, J. C.; Bickels, J.; Priebat, D.; Jelinek, J.; Kellar-Graney, K.; Shmookler, B.; Malawer, M. M. Am. Family Physician 2002, 65, 1123-1132.*
March, J. (1992). Advanced Organic Chemistry: Reactions, Mechanimsms, and Structure (pp. 898-900). Canada: John Wiley & Sons, Inc.*

(Continued)

*Primary Examiner*—Michael G. Hartley
*Assistant Examiner*—Kevin Capps
(74) *Attorney, Agent, or Firm*—Olga Mekhovich

(57) ABSTRACT

The compounds of the invention are represented by the following general structure

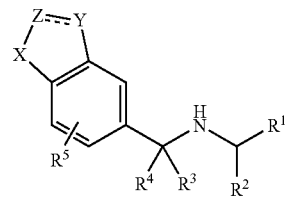

or a pharmaceutically acceptable salt thereof, and compositions containing them, wherein the variables are defined herein, and their use to reduce or inhibit PTH secretion, including methods for reducing or inhibiting PTH secretion and methods for treatment or prophylaxis of diseases associated with bone disorders, such as osteoporosis, or associated with excessive secretion of PTH, such as hyperparathyroidism. The subject invention also relates to processes for making such compounds as well as to intermediates useful in such processes.

12 Claims, No Drawings

OTHER PUBLICATIONS

Berge et al., "Pharmaceutical Salts," *J. Pharm. Sci.* 66(1):1-19 (1977).

Brown et al., "Neomycin Mimics the Effects of High Extracellular Calcium Concentrations on Parathyroid Function in Dispersed Bovine Parathyroid Cells," *Endocrinology* 128(6):3047-3054 (1991).

Bundgaard et al., "A Novel Solution-Stable, Water-Soluble Prodrug Type for Drugs Containing a Hydroxyl or an NH-Acidic Group," *J. Med. Chem.*, 32(12):2503-2507 (1989).

Chen et al., "The Diltiazem Analog TA-3090 Mimics the Actions of High Extracellular $Ca^{2+}$ on Parathyroid Function in Dispersed Bovine Parathyroid Cells," *J. Bone Miner. Res.* 5(6):581-587 (1990).

Dauban et al., "$N^1$-Arylsulfonyl-$N^2$-(1-aryl)ethyl-3-phenylpropane-1,2-diamines as Novel Calcimimetics Acting on the Calcium Sensing Receptor," *Bioorg. Med. Chem. Let.* 10(17):2001-2004 (2000).

Garrett et al., "Calcitonin-Secreting Cells of the Thyroid Express an Extracellular Calcium Receptor Gene," *Endocrinology* 136(11):5202-5211 (1995).

Garrett et al., "Molecular Cloning and Functional Expression of Human Parathyroid Calcium Receptor cDNAs," *J. Biol. Chem.* 270(21):12919-12925 (1995).

*J. Bone Miner. Res.* 9(Supple. 1):S282 (1994).

*J. Bone Miner. Res.* 9(Supple. 1):S409 (1994).

Kabalka et al., "The Reduction of Azides With Borohydride Supported on an Ion Exchange Resin," *Synth. Commun.*, 20(2):293-299 (1990).

Nemeth, "Regulation of Cytosolic Calcium by Extracellular Divalent Cations in C-cells and Parathyroid Cells," *Cell Calcium* 11:323-327 (1990).

Sande et al., "Borohydride Reducing Agent Derived From Anion Exchange Resin: Selective Reduction of $\alpha,\beta$-Unsaturated Carbonyl Compounds," *Tetrahedron Lett.* 25(32):3501-3504 (1984).

Svensson and Tunek, "The Design and Bioactivation of Presystemically Stable Prodrugs," *Drug Metabolsim Reviews* 19(2):165-194 (1988).

Zaidi, "Calcium Receptors' on Eukaryotic Cells with Special Reference to the Osteoclast," *Bioscience Reports* 10(6):493-507 (1990).

Woodruff et al., "Resonance Raman Spectra of Cobalt Myoglobins and Cobalt Porphyrins. Evaluation of Protein Effects on Porphyrin Structure," *J. Am. Chem. Soc.* 97(7):1695-1700 (1975).

U.S. Appl. No. 10/444,946, filed May 22, 2003, Kelly et al.

Nemeth et al. (1998), "Calcimimetics with potent and selective activity on the parathyroid calcium receptor," *Proc. Natl. Acad. Sci. USA* 95:4040-4045.

\* cited by examiner

CALCIUM RECEPTOR MODULATING AGENTS

This application claims the benefit of U.S. Provisional Application No. 60/383,270, filed May 23, 2002, which is hereby incorporated by reference.

BACKGROUND OF THE INVENTION

Extracellular calcium ion concentration is involved in a variety of biological processes, such as blood clotting, nerve and muscle excitability and bone formation (Cell Calcium 11:319, 1990). Calcium ion receptors, which are present on the membranes of various cells in the body, such as parathyroid and kidney cells (Nature 366:574, 1993; J. Bone Miner. Res. 9, Supple. 1, s282, 1994; J. Bone Miner. Res. 9, Supple. 1, s409, 1994; Endocrinology 136:5202, 1995), are important to the regulation of the extracellular calcium ion concentration. For example, concentration of extracellular calcium ion regulates the bone resorption by osteoclasts (Bioscience Reports 10:493, 1990), secretion of parathyroid hormone (PTH) from parathyroid cells and secretion of calcitonin from C-cells (Cell Calcium 11:323, 1990). Parathyroid hormone (PTH) is an important factor in regulating extracellular calcium ion concentration. Secretion of PTH increases extracellular calcium ion concentration by acting on various cells, such as bone and kidney cells, and the extracellular calcium ion concentration reciprocally inhibits the secretion of PTH by acting on parathyroid cells.

Several classes of calcimimetic compounds have been disclosed for regulating extracellular calcium ion concentration, particularly for reducing or inhibiting secretion of PTH. For example, EP 933354; WO 0021910, WO 96/12697; WO 95/11221; WO 94/18959; WO 93/04373; Endocrinology 128:3047, 1991; Biochem. Biophys. Res. commun. 167:807, 1990; J. Bone Miner. Res. 5:581, 1990; and Nemeth et al., "Calcium-binding Proteins in Health and Disease," Academix Press, Inc., pp. 33–35 (1987) disclose various agents which interact with calcium receptors.

Dauban et al., Bioorg. Med. Chem. Let. 10:2001–4, 2000, disclose various N1-arylsulfonyl-N2-(1-aryl)ethyl-3-phenylpropane-1,2-diamine compounds as calcimimetics acting on the calcium sensing receptor.

SUMMARY OF THE INVENTION

The present invention relates to selected calcimimetic compounds and pharmaceutically acceptable salts thereof. The invention compounds advantageously reduce or inhibit PTH secretion. Therefore, this invention also encompasses pharmaceutical compositions, methods for reducing or inhibiting PTH secretion and methods for treatment or prophylaxis of diseases associated with bone disorders, such as osteoporosis, or associated with excessive secretion of PTH, such as hyperparathyroidism. The subject invention also relates to processes for making such compounds as well as to intermediates useful in such processes.

The compounds of the invention are represented by the following general structure

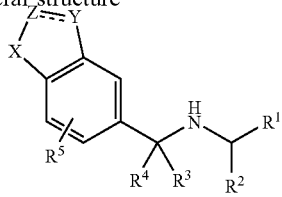

or a pharmaceutically acceptable salt thereof, wherein the variables are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

The invention provides compounds of Formula (I):

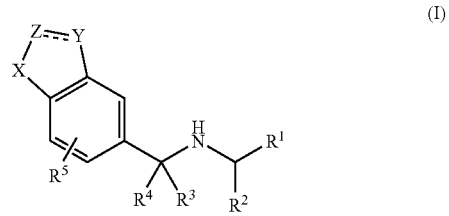

or a pharmaceutically acceptable salt thereof, wherein:

$\text{-----}$ represents a double or single bond;

$R^1$ is $R^b$;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$ or $NR^dC(=O)R^d$;

X is —$CR^d=N$—, —$N=CR^d$—, O, S or —$NR^d$—;

when $\text{-----}$ is a double bond then Y is =$CR^6$— or =N— and Z is —$CR^7$= or —N=; and when $\text{-----}$ is a single bond then Y is —$CR^aR^6$— or —$NR^d$— and Z is —$CR^aR^7$— or —$NR^d$—; and $R^6$ is $R^d$, $C_{1-4}$haloalkyl, —$C(=O)R^c$, —$OC_{1-6}$alkyl, —$OR^b$, —$NR^aR^a$, —$NR^aR^b$, —$C(=O)OR^c$, —$C(=O)NR^aR^a$, —$OC(=O)R^c$, —$NR^aC(=O)R^c$, cyano, nitro, —$NR^aS(=O)_mR^c$ or —$S(=O)_mNR^aR^a$;

$R^7$ is $R^d$, $C_{1-4}$haloalkyl, —$C(=O)R^c$, —$OC_{1-6}$alkyl, —$OR^b$, —$NR^aR^a$, —$NR^aR^b$, —$C(=O)OR^c$, —$C(=O)NR^aR^a$, —$OC(=O)R^c$, —$NR^aC(=O)R^c$, cyano, nitro, —$NR^aS(=O)_mR^c$ or —$S(=O)_mNR^aR^a$; or $R^6$ and $R^7$ together form a 3- to 6-atom saturated or unsaturated bridge containing 0, 1, 2 or 3 N atoms and 0, 1 or 2 atoms selected from S and O, wherein the bridge is substituted by 0, 1 or 2 substituents selected from $R^5$; wherein when $R^6$ and $R^7$ form a benzo bridge, then the benzo bridge may be additionally substituted by a 3- or 4-atoms bridge containing 1 or 2 atoms selected from N and O, wherein the bridge is substituted by 0 or 1 substituents selected from $C_{1-4}$alkyl;

$R^a$ is, independently, at each instance, H, $C_{1-4}$haloalkyl or $C_{1-6}$alkyl;

$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —C(=O)$R^c$, —$OR^b$, —$NR^aR^a$, —$NR^aR^b$, —C(=O)$OR^c$, —C(=O)$NR^aR^a$, —OC(=O)$R^c$, —$NR^aC$(=O)$R^c$, —$NR^aS$(=O)$_mR^c$ and —S(=O)$_mNR^aR^a$; and m is 1 or 2.

In one embodiment, in conjunction with any one of the above and below embodiments, $R^1$ is phenyl substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is benzyl substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is naphthyl substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is a saturated or unsaturated 5- or 6-membered ring heterocycle containing 1, 2 or 3 atoms selected from N, O and S, with no more than 2 of the atoms selected from O and S, wherein the heterocycle is substituted by 0, 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^3$ and $R^4$ are H.

In another embodiment, in conjunction with any one of the above and below embodiments, $R^5$ is H.

In another embodiment, in conjunction with any one of the above and below embodiments, $R^6$ is H.

In another embodiment, in conjunction with any one of the above and below embodiments, $R^7$ is H.

In another embodiment, in conjunction with any one of the above and below embodiments, X is —$NR^d$—.

In another embodiment, in conjunction with any one of the above and below embodiments:

-----is a double bond;

Y is =$CR^6$— or =N—; and

Z is —$CR^7$= or —N=.

In another embodiment, in conjunction with any one of the above and below embodiments:

-----is a single bond;

Y is —$CR^aR^6$— or —$NR^d$—; and

Z is —$CR^aR^7$— or —$NR^d$—.

In another embodiment, in conjunction with any one of the above and below embodiments, the invention provides a compound of Formula (II):

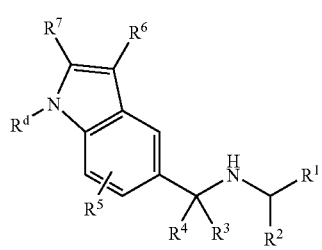

(II)

wherein:

$R^1$ is $R^b$;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$ or $NR^aC$(=O)$R^d$;

$R^6$ is $R^d$, $C_{1-4}$haloalkyl, —C(=O)$R^c$, —$OC_{1-6}$alkyl, —$OR^b$, —$NR^aR^a$, —$NR^aR^b$, —C(=O)$OR^c$, —C(=O)$NR^aR^a$, —OC(=O)$R^c$, —$NR^aC$(=O)$R^c$, cyano, nitro, —$NR^aS$(=O)$_mR^c$ or —S(=O)$_mNR^aR^a$;

$R^7$ is $R^d$, $C_{1-4}$haloalkyl, —C(=O)$R^c$, —$OC_{1-6}$alkyl, —$OR^b$, —$NR^aR^a$, —$NR^aR^b$, —C(=O)$OR^c$, —C(=O)$NR^aR^a$, —OC(=O)$R^c$, —$NR^aC$(=O)$R^c$, cyano, nitro, —$NR^aS$(=O)$_mR^c$ or —S(=O)$_mNR^aR^a$; or $R^6$ and $R^7$ together form a 3- to 6-atom saturated or unsaturated bridge containing 0, 1, 2 or 3 N atoms and 0, 1 or 2 atoms selected from S and O, wherein the bridge is substituted by 0, 1 or 2 substituents selected from $R^5$; wherein when $R^6$ and $R^7$ form a benzo bridge, then the benzo bridge may be additionally substituted by a 3- or 4-atoms bridge containing 1 or 2 atoms selected from N and O, wherein the bridge is substituted by 0 or 1 substituents selected from $C_{1-4}$alkyl;

$R^a$ is, independently, at each instance, H, $C_{1-4}$haloalkyl or $C_{1-6}$alkyl;

$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —C(=O)$R^c$, —$OR^b$, —$NR^aR^a$, —$NR^aR^b$, —C(=O)$OR^c$, —C(=O)$NR^aR^a$, —OC(=O)$R^c$, —$NR^aC$(=O)$R^c$, —$NR^aS$(=O)$_mR^c$ and —S(=O)$_mNR^aR^a$; and m is 1 or 2.

In another embodiment, in conjunction with any one of the above and below embodiments, the compound has the structure

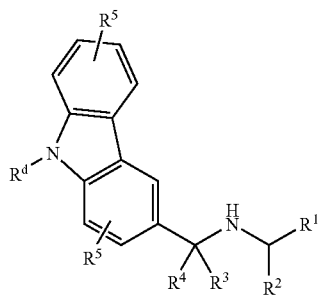

wherein:

$R^1$ is $R^b$;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$ or $NR^dC(=O)R^d$;

$R^a$ is, independently, at each instance, H, $C_{1-4}$haloalkyl or $C_{1-6}$alkyl;

$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —$C(=O)R^c$, —$OR^b$, —$NR^aR^a$, —$NR^aR^b$, —$C(=O)OR^c$, —$C(=O)NR^aR^a$, —$OC(=O)R^c$, —$NR^aC(=O)R^c$, —$NR^aS(=O)_mR^c$ and —$S(=O)_mNR^aR^a$; and m is 1 or 2.

In another embodiment, in conjunction with any one of the above and below embodiments, $R^1$ is phenyl substituted by 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is benzyl substituted by 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ is naphthyl substituted by 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, $R^1$ a saturated or unsaturated 5- or 6-membered ring heterocycle containing 1, 2 or 3 atoms selected from N, O and S, with no more than 2 of the atoms selected from O and S, wherein the heterocycle is substituted by 1, 2 or 3 substituents selected from $C_{1-6}$alkyl, halogen, $C_{1-4}$haloalkyl, —$OC_{1-6}$alkyl, cyano and nitro.

In another embodiment, in conjunction with any one of the above and below embodiments, one of $R^3$ or $R^4$ is $C_{1-4}$haloalkyl or $C_{1-8}$alkyl.

In another embodiment, in conjunction with any one of the above and below embodiments, $R^5$ is, independently, in each instance, $C_{1-8}$alkyl, $C_{1-4}$haloalkyl, halogen, —$OC_{1-6}$alkyl, —$NR^aR^d$ or $NR^dC(=O)R^d$.

In another embodiment, in conjunction with any one of the above and below embodiments, $R^6$ is not H.

In another embodiment, in conjunction with any one of the above and below embodiments, $R^7$ is not H.

Another aspect of the invention involves a pharmaceutical composition comprising a pharmaceutically acceptable amount of a compound according to any one of claims 1–22 and a pharmaceutically acceptable diluent or carrier.

Another aspect of the invention involves the use of a compound in conjunction with any one of the above and below embodiments, as a medicament.

Another aspect of the invention involves the use of a compound in conjunction with any one of the above and below embodiments, in the manufacture of a medicament for the treatment of diseases associated with bone disorders or associated with excessive secretion of PTH.

Another aspect of the invention involves the use of a compound in conjunction with any one of the above and below embodiments, in the manufacture of a medicament for the treatment of osteoporosis or hyperparathyroidism.

Another aspect of the invention involves a method of using a compound in conjunction with any one of the above and below embodiments, for the treatment of diseases associated with bone disorders or associated with excessive secretion of PTH.

Another aspect of the invention involves a method of using a compound in conjunction with any one of the above and below embodiments, for the treatment of osteoporosis or hyperparathyroidism.

Another aspect of the invention involves a process for making a compound in conjunction with any one of the above and below embodiments comprising the step of:

reacting a compound having the structure

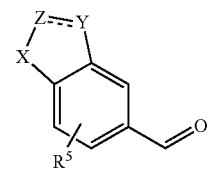

with an amine having the structure

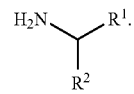

The compounds may also be synthesized as follows:

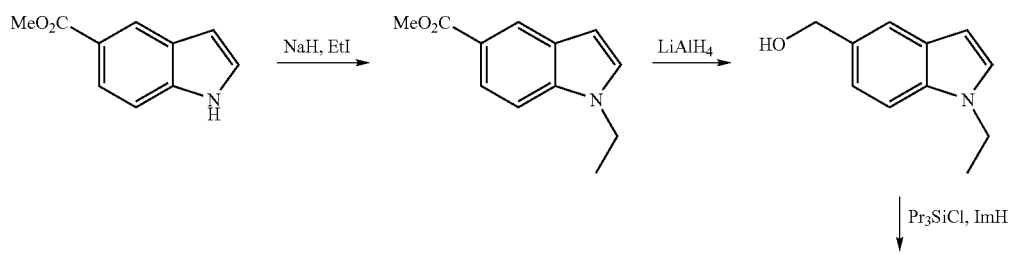

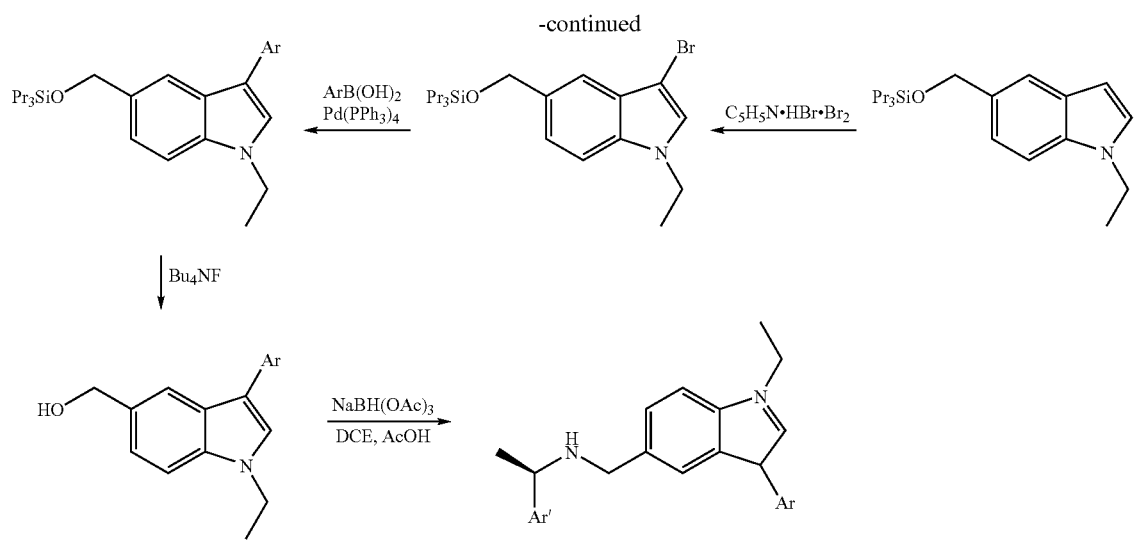

In the above reaction scheme, $C_5H_5N \cdot HBr \cdot Br_2$ is pyridinium hydrobromide perbromide; ImH is imidazole; and DCE is 1,2-dichloroethane Unless otherwise specified, the following definitions apply to terms found in the specification and claims:

"Alkyl" and the prefix "alk" refer to alkyl groups or substituents wherein the carbon atoms are in a branched, cyclical or linear relationship or any combination of the three. "$C_{v-w}$alkyl" means an alkyl group comprising from V to W carbon atoms. The alkyl groups described in this section contain from 1 to 10 carbon atoms unless otherwise specified and may also contain a double or triple bond. Examples of $C_{1-6}$ alkyl include, but are not limited to the following:

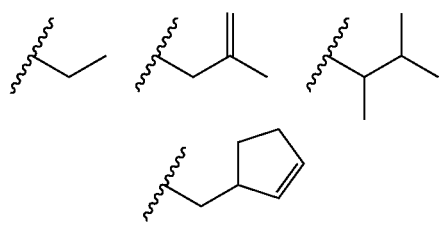

"Aryl" means a carbocyclic aromatic ring or ring system. Examples of aryl groups include phenyl, naphthyl, indenyl, anthrancenyl, 9-(9-phenylfluorenyl), phenanthrenyl, and the like.

"Halogen" means a halogen atom selected from F, Cl, Br and I.

"Haloalkyl", "haloalk-", and "$C_{v-w}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Heterocyclic groups can be saturated, unsaturated or aromatic. Aromatic heterocyclic groups are also referred to as "heteroaryl" rings or ring systems. Examples of heterocycles that may be found in the claims include, but are not limited to, the following:

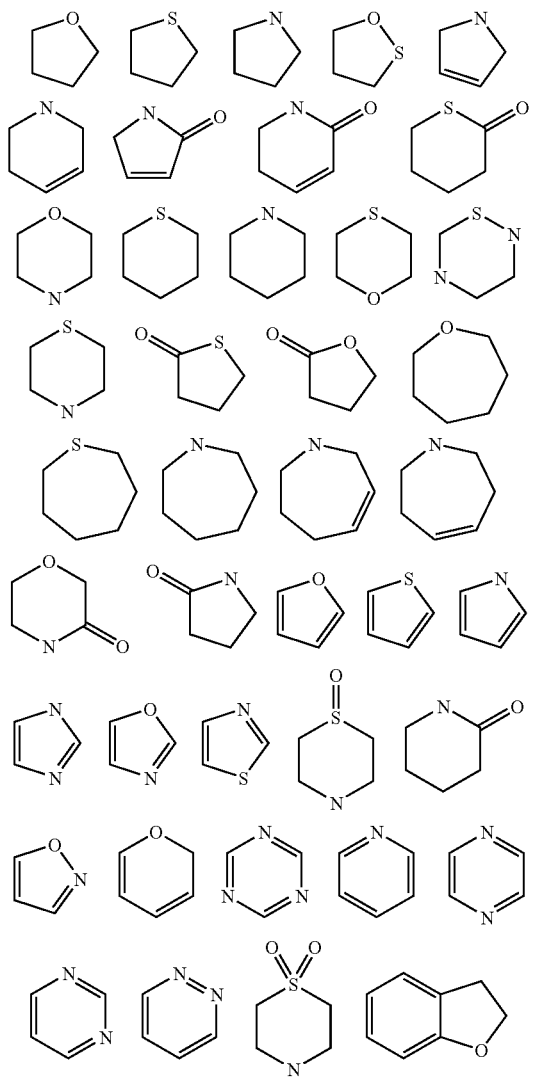

-continued

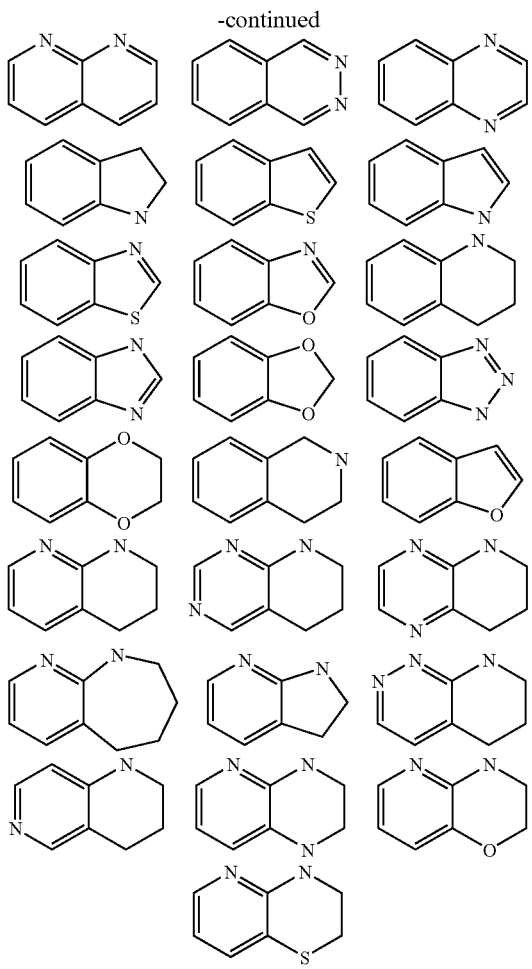

"Pharmaceutically acceptable salt" means a salt prepared by conventional means, and are well known by those skilled in the art. The "pharmaceutically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, orthomethylbenzyl, trityl and benzhydryl, which can be optionally substituted with halogen, alkyl, alkoxy, hydroxy, nitro, acylamino, acyl and the like, and salts, such as phosphonium and ammonium salts. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene) benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl) benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

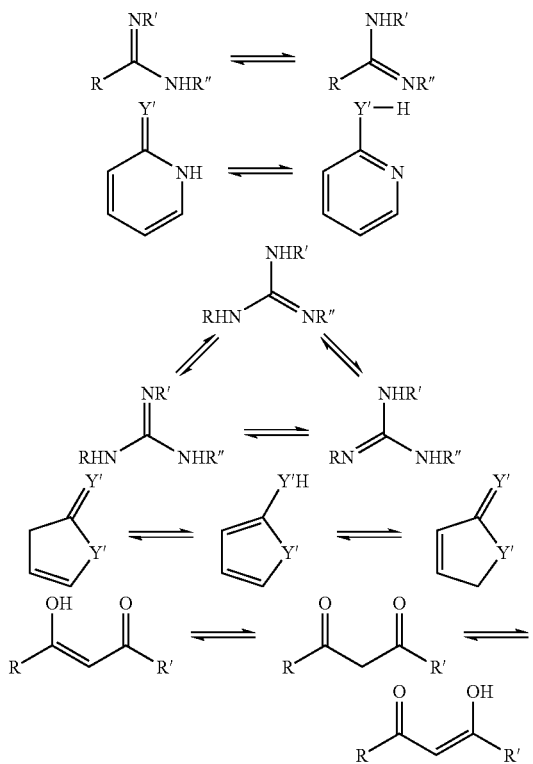

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known to those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Preferred compounds of the invention include:
(R)-N-(1-(1-Naphthyl)ethyl)-N-(9-ethyl-3-carbazolylmethyl)amine;
(R)-N-(1-(3-Methoxyphenyl)ethyl)-N-(9-ethyl-3-carbazolylmethyl)amine;
(R)-N-(1-(1-Naphthyl)ethyl)-N-(2'-ethyl-benzotriazol-5-ylmethyl)amine;
(R)-N-(1-((Phenyl)ethyl)-N-((1-ethylcyclopent[b]indol-5-yl)methyl)amine;
(R)-N-(1-(1-Naphthyl)ethyl)-N-(9-ethyl-3-carbazolylmethyl)amine;
(R)-N-(1-(3-Methoxyphenyl)ethyl)-N-(9-ethyl-3-carbazolylmethyl)amine;
(R)-N-(1-(Phenyl)ethyl)-N-(9-ethyl-3-carbazolylmethyl)amine;
(R)-N-(1-((1-naphthyl)ethyl)-N-((5-ethyl-5,6-dihydro-2H-pyrano[4,3-b]indol-8-yl)methyl)amine;
(1R)-N-((1-ethyl-3-phenyl-1H-indol-5-yl)methyl)-1-phenylethanamine;
(1R)-N-((1-ethyl-3-(3-((trifluoromethyl)oxy)phenyl)-1H-indol-5-yl)methyl)-1-(1-naphthalenyl)ethanamine;
(1R)-N-((1-ethyl-3-(3-(trifluoromethyl)phenyl)-1H-indol-5-yl)methyl)-1-1-naphthalenyl)ethanamine;
(1R)-N-((1-ethyl-3-(3-(trifluoromethyl)phenyl)-1H-indol-5-yl)methyl)-1-(3-(methyloxy)phenyl)ethanamine;
(1R)-1-(3-(methyloxy)phenyl)-N-((1-(4-(trifluoromethyl)phenyl)-1H-indol-5-yl)methyl)ethanamine; and pharmaceutically acceptable salts thereof.

Experimental

General Methods

In the following synthetic methods references to "the aldehyde" and "the amine" refer to the reaction of an aldehyde of the following formula:

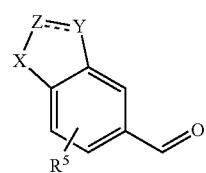

with an amine having the structure

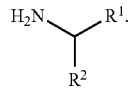

Method A The aldehyde (1.6 mmol) is dissolved in methanol (5 mL) and the amine (1.9 mmol) is added. The reaction is shaken for 24 hours or until imine formation is complete (as monitored by LCMS), then solid-supported borohydride is added (prepared according to Kabalka, G. W.; Wadgaonkar, P. P.; Chatla, N.; Synth. Commun.; (1990), 20 (2), 293–299) (ca 2.5 mmol/g; 3.1 mmol) and the mixture is shaken for 24 hours or until reduction is complete (as monitored by LCMS). Dichloromethane (ca 3 mL) is then added followed by Wang-aldehyde resin (4-benzyloxybenzaldehyde, polymer-bound; ca 1.25 mmol/g; 0.6 mmol) and the mixture is shaken for further 24 hours. The resins are filtered off and the solvents are evaporated under reduced pressure, to afford an oil which is purified by column chromatography (usually Hexane/AcOEt 7/3 or DCM/MeOH 95/5). The free-base oil is then treated with 1.5–2.5 mL 1N HCl in diethyl ether and the solvents are evaporated under reduced pressure to afford the mono or bis-HCl salt.

Method B The aldehyde (1.6 mmol) is dissolved in methanol (5 mL) and the amine (1.9 mmol) is added. The reaction is heated to reflux for 10 minutes then left to cool overnight until imine formation is complete (as monitored by LCMS). Solid-supported cyanoborohydride is added (prepared according to Sande, A. R.; Jagadale, M. H.; Mane, R. B.; Salunkhe, M. M.; *Tetrahedron Lett*. (1984), 25(32), 3501–4) (ca 2.5 mmol/g; 3.1 mmol) and the mixture is heated at 50° C. for 15 hours or until reduction is complete (as monitored by LCMS). Dichloromethane (ca 3 mL) is then added followed by Wang-aldehyde resin (4-benzyloxybenzaldehyde, polymer-bound; ca 1.25 mmol/g; 0.6 mmol) and the mixture is shaken for further 24 hours. The resins are filtered off and the solvents are evaporated under reduced pressure, to afford an oil which is purified by column chromatography (usually Hexane/AcOEt 7/3 or DCM/MeOH 95/5). The free-base oil is then treated with 1.5–2.5 mL 1N HCl in diethyl ether and the solvents are evaporated under reduced pressure to afford the mono or bis-HCl salt.

Method C The aldehyde (1.6 mmol) is dissolved in 1,2-dichloroethane (12 mL) and the amine (1.9 mmol) is added, followed by acetic acid (0.09 mL, 1.6 mmol) and finally sodium triacetoxyborohydride (500 mg, 2.4 mmol). The mixture is stirred overnight or until complete by TLC. Upon reaction completion, the mixture is diluted with ethyl acetate, washed with saturated NaHCO$_3$, then with saturated brine, and finally dried over sodium sulfate. The solvents are evaporated under reduced pressure, to afford an oil which is purified by column chromatography on silica gel (usually Hexane/AcOEt 7/3 or DCM/MeOH 95/5). The free-base oil is then treated with 1.5–2.5 1N HCl in diethyl ether and the solvents are evaporated under reduced pressure to afford the mono or bis-HCl salt.

EXAMPLE 1

(R)-N-(1-(1-Naphthyl)ethyl)-N-(9-ethyl-3-carbazolylmethyl)amine

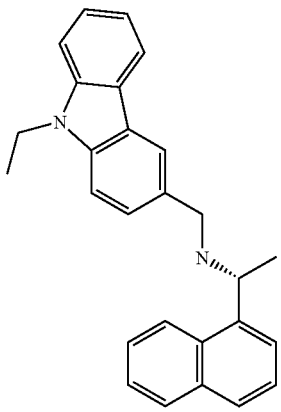

The title compound was prepared by the method C.

C$_{27}$H$_{26}$N$_2$O Mass (calculated): [378]. (found): [M+H$^+$]= 379. NMR (400 MHz, CDCl$_3$): 1.5 (3H, t, J=7 Hz, CH$_3$CH$_2$); 1.65 (3H, d, J=7 Hz, NCHCH$_3$); 3.9 and 4.0 (2H, dd, J=14 Hz, CH$_2$N); 4.4 (2H, q, J=7 Hz, CH$_3$CH$_2$); 4.85 (1H, q, J=7 Hz, NCHMe); 7.25 (1H, t, J=7 Hz, aryl-H); 7.35–7.55 (6H, m, aryl-H); 7.6 (1H, t, J=7 Hz, aryl-H); 7.85 (1H, d, J=7 Hz); 7.9–8 (2H, m, aryl-H); 8 (1H, s, aryl-H); 8.05 (1H, d, J=7 Hz, aryl-H); 8.2 (1H, bd, J=7 Hz; aryl-H).

EXAMPLE 2

(R)-N-(1-(3-Methoxyphenyl)ethyl)-N-(9-ethyl-3-carbazolylmethyl)amine

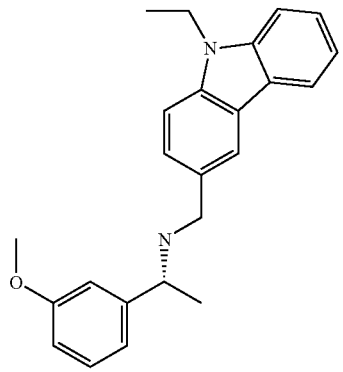

The title compound was prepared by the method C.

C$_{24}$H$_{26}$N$_2$O Mass (calculated): [358]. (found): [M+H$^+$]= 359. NMR (400 MHz, CDCl$_3$): 1.3–1.4 (6H, m, NCHCH$_3$ and CH$_2$CH$_3$); 3.7 (1H, d, J=12 Hz, CH$_2$N); 3.75–3.83 (5H, m, CH$_2$N, CHCH$_3$, OCH$_3$); 4.3 (2H, q, J=7 Hz, CH$_2$CH$_3$); 6.75 (1H, m, aryl-H); 6.9 (2H, m, aryl-H); 7.1–7.42 (6H, m, aryl-H); 7.9 (1H, s, aryl-H); 8.0 (1H, d, J=7 Hz, aryl-H).

EXAMPLE 3

(R)-N-(1-(1-Naphthyl)ethyl)-N-(1-ethyl-5-indolylmethyl)amine

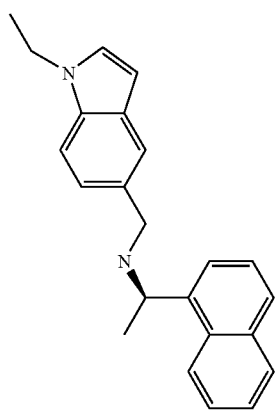

The title compound was prepared by the method C.

C$_{23}$H$_{24}$N$_2$ Mass (calculated): [328]. (found): [M+H$^+$]= 329, 157. NMR (400 MHz, CDCl$_3$): 1.29 (3H, t, J=7.6 Hz, CH$_2$CH$_3$); 1.39 (3H, d, J=6.6 Hz; CHCH$_3$); 3.67 and 3.76 (2H, dd, J=12.7 Hz, CH$_2$N); 4.0 (2H, q, J=7.6 Hz, CH$_2$CH$_3$); 4.6 (1H, q, J=6.6 Hz, CHCH$_3$); 6.32 (1H, d, J=3 Hz, indole-H); 6.95 (1H, d, J=3 Hz, indole-H); 7.05 (1H, dd, J=1.5 and 8 Hz, aryl-H); 7.16 (1H, d, J=8.6 Hz, aryl-H); 7.3–7.5 (3H, m, aryl-H); 7.63 (1H, d, J=7.6 Hz, aryl-H); 7.7–7.8 (2H, m, aryl-H); 8.0–8.1 (1H, m, aryl-H).

EXAMPLE 4

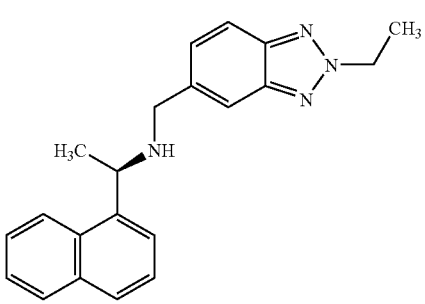

Example 4A

Ethyl 2-ethylbenzotriazole-5-carboxylate

Benzotriazole-5-carboxylic acid (1.5 g, 9.2 mmol) and ethyl iodide (1.61 mL, 20.2 mmol) were dissolved in DMF (20 mL and sodium hydride (0.800 g, 20.2 mmol, 60% suspension in mineral oil) was added. The mixture was stirred under nitrogen at 55° C. for one hour then the reaction was cooled and quenched with water, diluted with ethyl acetate and washed with water. The organic phase was separated and dried over sodium sulfate. The crude was purified by column chromatography (ethyl acetate/hexane 3/2 and the major isomer isolated (0.76 g) was tentatively assigned as the title compound (cfr also Palmer, M. H., Findlay, R. H. et al. *J. Chem. Soc. Perkin Trans.* 2, 1975, 1695–1700).

$C_{11}H_{13}N_3O_2$ Mass (calculated): [219]. (found): [M+H$^+$]= 220. NMR (400 MHz, CDCl$_3$): 1.3 (3H, t, J=7 Hz, CH$_2$CH$_3$); 1.6 (3H, t, J=7 Hz, CH$_2$CH$_3$); 4.3 (2H, q, J=7 Hz, CH$_2$CH$_3$); 4.7 (2H, q, J=7 Hz, CH$_2$CH$_3$); 7.8 (1H, d, J=8.5 Hz, aryl-H); 7.95 (1H, d, J=8.5 Hz, aryl-H); 8.6 (1H, s, aryl-H).

Example 4B

2-Ethyl-5-hydroxymethylbenzotriazole

Ethyl 2-ethylbenzotriazole-5-carboxylate (0.7 g, 3.06 mmol) was dissolved in dry toluene (10 mL) and cooled to 0° C. under nitrogen. A solution of DIBAL-H (1.5M in toluene, 3 mL, 4.5 mmol) was then added dropwise to the cooled solution over 15 minutes. The reaction was stirred at 0° C. for one hour when further DIBAL-H (1.5 mL, 2.25 mmol) was added. A further aliquot of DIBAL-H (0.75 mL, 1.12 mmol) was added after 2 hours and the reaction was stirred for further 30 min. The reaction was quenched by addition of a saturated solution of sodium potassium tartrate, diluted with water and extracted with AcOEt. The organic layer was dried over sodium sulfate to give a crude oil (440 mg) which was used directly in the following step.

$C_9H_{11}N_3O$ Mass (calculated): [177]. (found): [M+H$^+$]= 178. NMR (400 MHz, CDCl$_3$): 1.6 (3H, t, J=7 Hz, CH$_2$CH$_3$); 4.65 (2H, q, J=7 Hz, CH$_2$CH$_3$); 4.75 (2H, s, CH$_2$O); 7.25 (1H, dd, J=8.5 and 2 Hz, aryl-H); 7.7–7.75 (1H, m, aryl-H); 7.75 (1H, s, aryl-H).

Example 4C

2-Ethyl-5-formylbenzotriazole

The crude alcohol from the previous step (440 mg, 2.49 mmol) was dissolved in acetone (10 mL) and treated with manganese dioxide (2.6 g, 29.9 mmol). The reaction was stirred at room temperature for 72 hours then the solid filtered off to afford the aldehyde which was used without further purification $C_9H_9N_3O$ Mass (calculated): [175]. (found): [M+H$^+$]= 176. NMR (400 MHz, CDCl$_3$): 1.6 (3H, t, J=7 Hz, CH$_2$CH$_3$); 4.75 (2H, q, J=7 Hz, CH$_2$CH$_3$); 7.8–7.85 (2H, m, aryl-H); 8.2 (1H, s, aryl-H); 9.8 (1H, s, CHO)

Example 4D (R)-N-(1-(1-Naphthyl)ethyl)-N-(2'-ethyl-benzotriazol-5-ylmethyl)amine Prepared according to General Procedure C.

$C_{21}H_{22}N_4$ Mass (calculated): [330]. (found): [M+H$^+$]= 155, 331. NMR (400 MHz, CDCl$_3$): 1.45 (3H, d, J=7 Hz, CH$_3$CHN); 1.65 (3H, t, J=7 Hz, CH$_3$CH$_2$N); 3.75 and 3.8 (2H, dd, J=12 Hz, aryl-CH$_2$N); 4.6–4.7 (3H, m, aryl-CHCH$_3$ and CH$_2$CH$_3$); 7.25 (1H, dd, J=8.5 and 2 Hz, aryl-H); 7.35–7.4 (3H, m, aryl-H); 7.7–7.75 (4H, m, aryl-H); 7.75–7.8 (1H, m, aryl-H); 8.05–8.1 (1H, m, aryl-H).

EXAMPLE 5

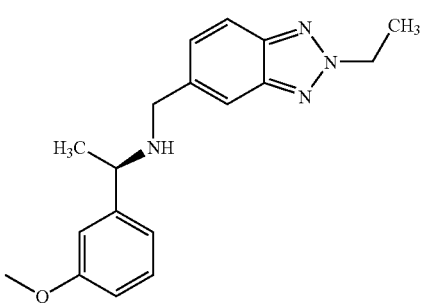

(R)-N-(1-(3-Methoxyphenyl)ethyl)-N-(2'-ethyl-benzotriazol-5-ylmethyl)amine

Prepared according to General Procedure C.

$C_{18}H_{22}N_4O$ Mass (calculated): [310]. (found): [M+H$^+$]= 311. NMR (400 MHz, CDCl$_3$): 1.3 (3H, d, J=7 Hz, CH$_3$CHN); 1.65 (3H, t, J=7 Hz, CH$_3$CH$_2$N); 3.6–3.85 (6H, m, CH$_3$O, aryl-CHCH$_3$ and aryl-CH$_2$N); 4.65–4.75 (2H, m, CH$_2$CH$_3$); 7.7–6.75 (1H, m, aryl-H); 6.85–6.9 (2H, m, aryl-H); 7.15–7.25 (1H, m, aryl-H); 7.25–7.3 (1H, m, aryl-H); 7.65 (1H, s, aryl-H); 7.75–7.8 (1H, m, aryl-H).

EXAMPLE 6

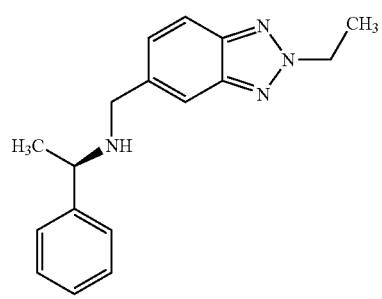

(R)-N-(1-(Phenyl)ethyl)-N-(2'-ethyl-benzotriazol-5-ylmethyl)amine

Prepared according to General Procedure C.

$C_{17}H_{20}N_4$ Mass (calculated): [280]. (found): [M+H$^+$]= 281. NMR (400 MHz, CDCl$_3$): 1.3 (3H, d, J=7 Hz, CH$_3$CHN); 1.65 (3H, t, J=7 Hz, CH$_3$CH$_2$N); 3.6 and 3.7 (2H, dd, J=12 Hz, aryl-CH$_2$N); 3.75 (1H, q, J=7 Hz, NCHCH$_3$); 4.7 (2H, q, J=7 Hz, CH$_2$CH$_3$); 7.15–7.2 (1H, m, aryl-H); 7.20–7.30 (5H, m, aryl-H); 7.65 (1H, s, aryl-H); 7.7 (1H, d, J=8 Hz, aryl-H).

EXAMPLE 7

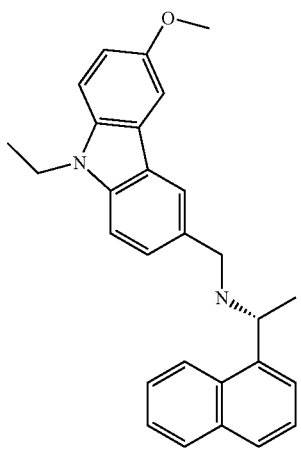

Example 7A

6-Methoxy-1,2,3,4-tetrahydrocarbazole-3-carboxylic acid ethyl ester

A solution of ethyl 4-oxocyclohexanecarboxylate (3 g, 17.6 mmol) and sodium acetate (1.59 g, 19.4 mmol) in glacial acetic acid (36 mL) was degassed with nitrogen prior to addition of 4-methoxyphenylhydrazine hydrochloride (3.38 g, 19.4 mmol). The mixture was heated at reflux for 2 hours then cooled, poured into water and extracted with tert-butylmethyl ether. The organic phase was washed with 5% $K_2CO_3$, then water and finally brine. The organic layer was dried over sodium sulphate then solvent removed under reduced pressure and the residue purified by column chromatography to afford 3.29 g of the title compound.

$C_{16}H_{19}NO_3$ Mass (calculated): [273]. (found): [M+H$^+$]= 274. NMR (400 MHz, CDCl$_3$): 1.22 (3H, t, J=6 Hz, CH$_3$CH$_2$O); 1.85–2.0 (1H, m, cyclohexenyl-H); 2.2–2.3 (1H, m, cyclohexenyl-H); 2.65–2.85 (4H, m, cyclohexenyl-H); 2.9–3.0 (1H, m, cyclohexenyl-H); 3.75 (3H, s, CH$_3$O); 4.15 (2H, q, J=6 Hz, OCH$_2$CH$_3$); 6.7 (1H, dd, J=2 and 8 Hz, aryl-H); 6.85 (1H, d, J=2 Hz, aryl-H); 7.1 (1H, d, J=8 Hz, aryl-H); 7.55 (1H, bs, NH).

Example 7B

6-Methoxycarbazole-3-carboxylic acid ethyl ester

A solution of 6-methoxy-1,2,3,4-tetrahydrocarbazole-3-carboxylic acid ethyl ester (3.29 g, 12.1 mmol) in p-cymene (12 mL) was treated with palladium (10% on carbon, 2.25 g) and heated at 190° C. for 20 hours. The mixture was then cooled, diluted with dichloromethane and filtered over a pad of diatomaceous earth. The filtrate was concentrated in vacuo to a low volume and heptane (200 mL) was added to precipitate the title compound as a white solid (2.78 g).

$C_{16}H_{15}NO_3$ Mass (calculated): [269]. (found): [M+H$^+$]= 270. NMR (400 MHz, CDCl$_3$): 1.4 (3H, t, J=6 Hz, CH$_3$CH$_2$O); 3.85 (3H, s, CH$_3$O); 4.4 (2H, q, J=6 Hz, OCH$_2$CH$_3$); 7.0 (1H, dd, J=2 and 8 Hz, aryl-H); 7.3 (1H, d, J=8 Hz, aryl-H); 7.35 (1H, d, J=8 Hz, aryl-H); 7.55 (1H, d, J=2 Hz, aryl-H); 8.05 (1H, dd, J=1 and 8 Hz); 8.15 (1H, bs, NH); 8.7 (1H, d, J=1 Hz, aryl-H).

Example 7C

9-Ethyl-6-methoxycarbazole-3-carboxylic acid ethyl ester

A solution of 6-methoxycarbazole-3-carboxylic acid ethyl ester (1.28 g, 4.77 mmol) in DMF (8 mL) was added to a suspension of sodium hydride (60% in mineral oil, 0.286 mg, 7.15 mmol) in DMF at 0° C. The reaction was stirred for 30 minutes then ethyl iodide was added (0.89 g, 5.72 mmol). The reaction was allowed to reach room temperature and was stirred for further 15 hours then was diluted with NH$_4$Cl sat. and water. The reaction was extracted with tert-butylmethyl ether and the organic phase was washed with water then brine. The organic layer was dried over sodium sulfate and the solvent concentrated in vacuo to give a crude which was purified by column (10% ethyl acetate/hexane) to afford 0.79 g of the title compound.

$C_{18}H_{19}NO_3$ Mass (calculated): [297]. (found): [M+H$^+$]= 298. NMR (400 MHz, CDCl$_3$): 1.35–1.45 (6H, m, CH$_3$CH$_2$O and CH$_3$CH$_2$N); 3.9 (3H, s, CH$_3$O); 4.3 (2H, q, J=6 Hz, NCH$_2$CH$_3$); 4.4 (2H, q, J=6 Hz, OCH$_2$CH$_3$); 7.1 (1H, dd, J=2 and 8 Hz, aryl-H); 7.32 (1H, d, J=8 Hz, aryl-H); 7.35 (1H, d, J=8 Hz, aryl-H); 7.55 (1H, d, J=2 Hz, aryl-H); 8.1 (1H, dd, J=1 and 8 Hz); 8.15 (1H, bs, NH); 8.7 (1H, d, J=1 Hz, aryl-H).

Example 7D

9-Ethyl-3-hydroxymethyl-6-methoxycarbazole

A solution of 9-ethyl-6-methoxycarbazole-3-carboxylic acid ethyl ester (1.36 g, 4.58 mmol) in anhydrous THF was added to a solution of lithium aluminum hydride in THF (25 mL) at 0° C. The reaction was stirred for 1 hour then water (1 mL) was added followed by 2M NaOH (1 mL) and finally water (1 mL). The reaction was then filtered on diatomaceous earth and the filtrate was dried and solvent removed in vacuo to afford 0.79 g of the crude alcohol.

$C_{16}H_{17}NO_2$ Mass (calculated): [255]. (found): [M+H$^+$]= 238, 255.

Example 7E

9-Ethyl-6-methoxycarbazole-3-carboxaldehyde

A solution of 9-ethyl-3-hydroxymethyl-6-methoxycarbazole (0.305 g, 1.2 mmol) in acetone (5 mL) was treated with MnO$_2$ (0.52 g, 6 mmol) and the reaction stirred at room temperature for 60 hours. The reaction mixture was filtered and the solvent evaporated under reduced pressure. The crude was purified by column chromatography (heptane/ethyl acetate 5/1) to afford 0.190 mg of the title compound.

$C_{18}H_{19}NO_3$ Mass (calculated): [253]. (found): [M+H$^+$]= 254. NMR (400 MHz, CDCl$_3$): 1.3 (3H, t, J=6 Hz, CH$_3$CH$_2$N); 3.85 (3H, s, CH$_3$O); 7.1 (1H, dd, J=2 and 8 Hz, aryl-H); 7.3 (1H, d, J=8 Hz, aryl-H); 7.35 (1H, d, J=8 Hz, aryl-H); 7.55 (1H, d, J=2 Hz, aryl-H); 7.9 (1H, dd, J=1 and 8 Hz); 8.4 (1H, d, J=1 Hz, aryl-H); 10 (1H, s, CHO).

Example 7F (R)-N-(1-(1-Naphthyl)ethyl)-N-(9-ethyl-6-methoxy-3-carbazolylmethyl)amine Prepared according to general procedure C.
$C_{28}H_{28}N_2O$ Mass (calculated): [408]. (found): [M+H$^+$]= 238, 409. NMR (400 MHz, CDCl$_3$): 1.3 (3H, t, J=6 Hz, CH$_3$CH$_2$N); 1.45 (3H, d, J=6 Hz, CH$_3$CHN); 3.8 (1H, d, J=12 Hz, aryl-CH$_2$N); 3.85 (3H, s, CH$_3$O); 3.9 (1H, d, J=12 Hz, aryl-CH$_2$N); 4.25 (1H, q, J=6 Hz, NCH$_2$CH$_3$); 4.7 (1H, q, J=6 Hz, CH₃CHN); (7.1 (1H, dd, J=2 and 8 Hz, aryl-H); 7.3 (1H, d, J=8 Hz, aryl-H); 7.35 (1H, d, J=8 Hz, aryl-H); 7.4–7.45 (1H, m, aryl-H); 7.5–7.55 (3H, m, aryl-H); 7.7 (1H, d, J=8 Hz, aryl-H); 7.75 (1H, d, J=8 Hz, aryl-H); 7.8–7.9 (2H, m, aryl-H); 8–8.1 (1H, m, aryl-H).

EXAMPLE 8

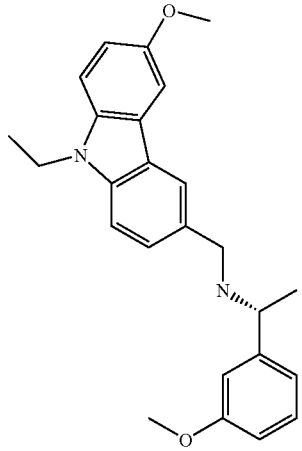

(R)-N-(1-(3-Methoxyphenyl)ethyl)-N-(9-ethyl-6-methoxy-3-carbazolylmethyl)amine

Prepared according to general procedure C.

$C_{25}H_{28}N_2O_2$ Mass (calculated): [388]. (found): [M+H⁺]= 238, 389, 777. NMR (400 MHz, CDCl₃): 1.3–1.4 (6H, m, CH₃CH₂N and CH₃CHN); 3.7 (1H, d, J=12 Hz, aryl-CH₂N); 3.75–3.85 (5H, m, CH₃O, aryl-CH₂N, CH₃CHN); 4.25 (1H, q, J=6 Hz, NCH₂CH₃); 6.85 (1H, dd, J=2 and 8 Hz, aryl-H); 6.9–6.95 (2H, m, aryl-H); 7.1 (1H, dd, J=2 and 8 Hz, aryl-H); 7.25–7.35 (4H, m, aryl-H); 7.5 (1H, d, J=2 Hz, aryl-H); 7.9 (1H, s, aryl-H).

EXAMPLE 9

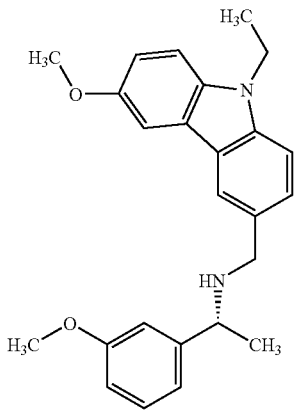

(R)-N-(1-((Phenyl)ethyl)-N-(9-ethyl-6-methoxy-3-carbazolylmethyl)amine

Prepared according to general procedure C.

$C_{24}H_{26}N_2O$ Mass (calculated): [358]. (found): [M+H⁺]= 238, 359. NMR (400 MHz, CDCl₃): 1.3–1.35 (6H, m, CH₃CH₂N and CH₃CHN); 3.7 (1H, d, J=12 Hz, aryl-CH₂N); 3.75 (7 (1H, d, J=12 Hz, aryl-CH₂N); 3.8 (1H, q, J=6 Hz, CH₃CHN); 3.85 (3H, s, CH₃O); 4.25 (1H, q, J=6 Hz, NCH₂CH₃); 7.1 (1H, dd, J=2 and 8 Hz, aryl-H); 7.25–7.4 (8H, m, aryl-H); 7.5 (1H, d, J=2 Hz, aryl-H); 7.9 (1H, s, aryl-H)

EXAMPLE 10

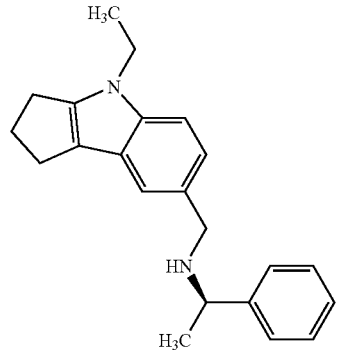

(R)-N-(1-((Phenyl)ethyl)-N-((1-ethylcyclopent[b]indol-5-yl)methyl)amine

Example 10A

5-Cyanocyclopent[b]indole

A solution of cyclopentanone (1 g, 12.0 mmol), 4-cyanophenylhydrazine hydrochloride (2.2 g, 13.1 mmol) and sodium acetate (1.07 g, 13 mmol) in glacial acetic acid (20 mL) was refluxed 2 hours then cooled and poured into water and extracted with dichloromethane. The organic layer was washed with NaHCO₃ sat. and water, then dried over sodium sulfate and solvent removed in vacuo. The crude was purified by column chromatography (40/60 ethyl acetate/hexane) to give 980 mg of title compound.

$C_{12}H_{12}N_2$ Mass (calculated): [182]. (found): [M+H⁺]= 183. NMR (400 MHz, CDCl₃): 2.45–2.55 (2H, m, cyclopentyl-H); 2.75–2.85 (4H, m, cyclopentyl-H); 7.3 (2H, s, aryl-H); 7.8 (1H, s, aryl-H); 8.1 (1H, bs, NH).

Example 10B

5-Cyano-1-ethylcyclopent[b]indole

A solution of 7-cyano-1,2,3,4-tetrahydrocyclopent[b]indole (0.224 g, 1.23 mmol) in anhydrous DMF (15 mL) was cooled to 0° C. and sodium hydride (60% dispersion in mineral oil, 74 mg, 3.07 mmol) was added. The reaction was stirred for 45 minutes then ethyl iodide (0.171 g, 1.47 mmol) was added and the reaction was allowed to warm to room temperature. The mixture was stirred for 15 hours then water was added. The product precipitated and was collected by filtration, washing with little water, brine and dichloromethane to give 0.287 g of title compound.

$C_{14}H_{14}N_2$ Mass (calculated): [210]. (found): [M+H⁺]= 211. NMR (400 MHz, CDCl₃): 1.3 (3H, t, J=2 Hz, CH₃CH₂N); 2.45–2.6 (2H, m, cyclopentyl-H); 2.75–2.9 (4H, m, cyclopentyl-H); 4.1 (1H, q, J=6 Hz, NCH₂CH₃); 7.2–7.3 (2H, m, aryl-H); 7.7 (1H, s, aryl-H)

Example 10C 1-ethylcyclopent[b]indole-5-carboxaldehyde

A solution of 7-cyano-4-ethyl-1,2,3,4-tetrahydrocyclopent[b]indole (0.28 g, 1.33 mmol) in dichloromethane (15 mL) was cooled in an ice-bath then treated with DIBAL-H (0.189 g, 1.33 mmol). The reaction was then allowed to reach room temperature and was stirred for 15 hours before diluting with dichloromethane and pouring into a saturated solution of sodium potassium tartrate. The organic layer was separated then washed with brine. The crude product was purified by column chromatography eluting with dichloromethane, to afford 0.2 g of title compound.

$C_{14}H_{15}NO$ Mass (calculated): [213]. (found): [M+H$^+$]= 214. NMR (400 MHz, CDCl$_3$): 1.3 (3H, t, J=2 Hz, CH$_3$CH$_2$N); 2.45–2.55 (2H, m, cyclopentyl-H); 2.75–2.85 (4H, m, cyclopentyl-H); 4.1 (1H, q, J=6 Hz, NCH$_2$CH$_3$); 7.3 (1H, d, J=8 Hz, aryl-H); 7.75 (1H, dd, J=1 and 8 Hz, aryl-H), 7.9 (1H, d, J=1 Hz, aryl-H); 9.7 (1H, s, CHO)

Example 10D (R)-N-(1-((Phenyl)ethyl)-N-((1-ethylcyclopent[b]indol-5-yl)methyl)amine Prepared according to general procedure C.

$C_{22}H_{26}N_2$ Mass (calculated): [318]. (found): [M+H$^+$]= 198, 319. NMR (400 MHz, CDCl$_3$): 1.2–1.3 (6H, m, (6H, m, CH$_3$CH$_2$N and CH$_3$CHN); 2.4-2.5 (2H, m, cyclopentyl-H); 2.75–2.85 (4H, m, cyclopentyl-H); 3.55 (1H, d, J=12 Hz, aryl-CH$_2$N); 3.65 (1H, d, J=12 Hz, aryl-CH$_2$N); 3.75 (1H, 2, (1H, d, J=6 Hz, CH$_3$CHN); 3.95 (2H, q, NCH$_2$CH$_3$); 6.9 (1H, dd, (1H, d, J=2 and 8 Hz, aryl-H); 7.1 (1H, d, (1H, d, J=8 Hz, aryl-H); 7.2–7.3 (1H, m, aryl-H); 7.3–7.4 (5H, m, aryl-H)

EXAMPLE 11

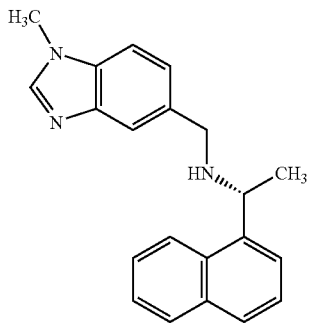

(R)-N-(1-(1-Naphthyl)ethyl)-N-((1-methylbenzimidazol-5-yl)methyl)amine

Example 11A

Methyl 1-methylbenzimidazole-5-carboxylate

A solution of methyl 3-amino-4-methylaminobenzoate (prepared as in DE 1990390463 A1) (2.57 g, 14 mmol) in trimethyl orthoformate (50 mL) was refluxed for 16 hours. The solvent was then removed under reduced pressure to afford 2.31 g of product.

$C_{10}H_{10}N_2O_2$ Mass (calculated): [190]. (found): [M+H$^+$]= 191. NMR (400 MHz, dmso-d$_6$): 3.95 (3H, s, NCH$_3$); 4.0 (3H, s, OCH$_3$); 7.8 (1H, d, J=8 Hz, aryl-H); 8.0 (1H, dd, J=1 and 8 Hz, aryl-H); 8.35 (1H, d, J=1 Hz, aryl-H); 8.45 (1H, s, imidazole-H).

Example 11B

5-Hydroxymethyl-1-methylbenzimidazole

A solution of methyl 1-methylbenzimidazole-5-carboxylate (1.6 g, 8.42 mmol) in dry THF (80 mL) was treated with LiAlH$_4$ (1.59 g, 42.1 mmol) and the mixture stirred for 2 hours. 1.5 mL of 5% NaOH solution was then added, and the solid which precipitated was filtered through diatomaceous earth. The filtrate was collected and the solvent removed under reduced pressure to give 0.8 g of the title compound.

$C_9H_{10}N_2O$ NMR (400 MHz, DMSO-d$_6$): 3.85 (3H, s, NCH$_3$); 4.65 (2H, s, CH$_2$OH); 5.25 (1H, bs, OH); 7.3 (1H, dd, J=1 and 8 Hz, aryl-H); 7.55 (1H, d, J=8 Hz, aryl-H); 7.65 (1H, d, J=1 Hz, aryl-H); 8.2 (1H, s, imidazole-H)

Example 11C

1-Methylbenzimidazole-5-carboxaldehyde

A solution of 5-hydroxymethyl-1-methylbenzimidazole (0.8 g, 4 mmol) in acetone (40 mL) was treated with MnO$_2$ (4 g) and the mixture was stirred for 3 days. The solid was filtered off and the solvent removed under reduced pressure to give 0.63 g of product.

$C_9H_8N_2O$ Mass (calculated): [160]. (found): [M+H$^+$]= 161. NMR (400 MHz, dmso-d$_6$): 3.95 (3H, s, NCH$_3$); 7.8 (1H, d, J=8 Hz, aryl-H); 7.9 (1H, dd, J=1 and 8 Hz, aryl-H); 8.3 (1H, d, J=1 Hz, aryl-H); 8.45 (1H, s, imidazole-H); 10.1 (1H, s, CHO).

Example 11D (R)-N-(1-(1-naphthyl)ethyl)-N-((1-methylbenzimidazol-5-yl)methyl)amine Prepared according to general procedure C.

$C_{21}H_{21}N_3$ Mass (calculated): [315]. (found): [M+H$^+$]= 316, 155, 631. NMR (400 MHz, CDCl$_3$): 1.55 (3H, d, J=7 Hz, CH$_3$CHN); 3.7–3.8 (4H, m, imidazole NCH$_3$ and aryl-CH$_2$N); 3.95 (1H, d, J=11 Hz, aryl-CH$_2$N); 4.05 (1H, q, J=7 Hz, NCHCH$_3$); 7.25–7.35 (2H, m, aryl-H); 7.45–7.55 (3H, m, aryl-H); 7.75–7.85 (3H, m, aryl-H); 7.85–7.95 (2H, m, aryl-H); 8.15–8.25 (1H, m, aryl-H).

EXAMPLE 12

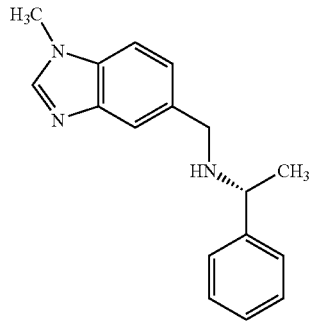

(R)-N-(1-(Phenyl)ethyl)-N-((1-methylbenzimidazol-5-yl)methyl)amine

Prepared according to general procedure C.

$C_{17}H_{19}N_3$ Mass (calculated): [265]. (found): [M+H$^+$]= 266, 531. NMR (400 MHz, CDCl$_3$): 1.3 (3H, d, J=7 Hz, CH$_3$CHN); 3.65 (1H, d, J=11 Hz, aryl-CH$_2$N); 3.7–3.8 (5H, m, imidazole NCH$_3$, CH$_3$CHN and aryl-CH$_2$N); 7.1–7.3 (7H, m, aryl-H); 7.6 (1H, s, aryl-H); 7.8 (1H, s, aryl-H).

EXAMPLE 13

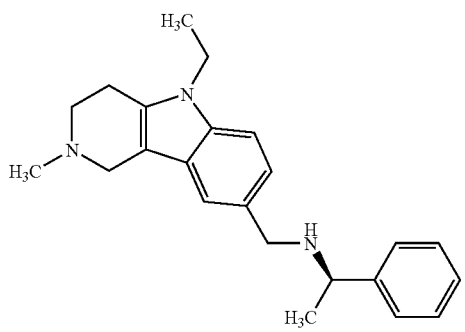

(R)-N-(1-((Phenyl)ethyl)-N-((5-ethyl-2-methyl-1,2,5,6-tetrahydropyrido[3,4-b]indole-8-yl)methyl)amine Example 13A 2-Ethoxycarbonyl-1,2,5,6-tetrahydropyrido[3,4-b]indole-8-carboxylic acid A 20 mL pressure tube was charged with 4-carboxyphenylhydrazine (0.32 g, 2.1 mmol), 1-ethoxycarbonyl-4-piperidone (0.34 g, 2.0 mmol) and acetic acid (4 mL). The suspension was heated with stirring for 2 minutes at 100 W in a microwave oven to form the hydrazone intermediate. Polyphosphoric acid was then added (1 g) and the resulting yellow suspension was heated in the microwave oven for 2 minutes and then for further 2 minutes at 100 W. The reaction mixture was then poured into hot water (30 mL) and the product separated as a gray solid (0.37 g).

$C_{15}H_{16}N_2O_4$ Mass (calculated): [288]. (found): [M+H$^+$]= 289. NMR (400 MHz, dmso-d$_6$): 1.2 (3H, d, J=6 Hz, CH$_3$CH$_2$O); 2.75–2.85 (2H, m, CCH$_2$CH$_2$N); 3.7–3.8 (2H, m, CCH$_2$CH$_2$N); 4.05 (2H, q, J=6 Hz, CH$_3$CH$_2$O); 4.55–4.65 (2H, m, CCH$_2$N); 7.35 (1H, d, J=8 Hz, aryl-H); 7.7 (1H, dd, J=1 and 8 Hz, aryl-H); 8.1 (1H, d, J=1 Hz, aryl-H).

Example 13B

Ethyl 5-ethyl-2-ethoxycarbonyl-1,2,5,6-tetrahydropyrido[3,4-b]indole-8-carboxylate A solution of 2-ethoxycarbonyl-1,2,3,4-tetrahydropyrido[4,3-b]indole-8-carboxylic acid (0.35 g, 1.22 mmol) in dry DMF (10 mL) was cooled to 0° C. and sodium hydride (60% suspension in mineral oil, 0.122 g, 3.04 mmol) was added and the mixture was stirred for 30 minutes. Ethyl iodide (0.21 mL, 2.68 mmol) was then added and the reaction was allowed to reach room temperature and was stirred for further 24 hours. The reaction mixture was then diluted with ethyl acetate and water and extracted. The organic layer was washed with brine, dried over sodium sulfate, and the solvent removed under reduced pressure to give a crude which was purified by column chromatography (DCM/MeOH 98/2) to afford 0.367 g of the title compound.

$C_{19}H_{24}N_2O_4$ Mass (calculated): [344]. (found): [M+H$^+$]= 345. NMR (400 MHz, CDCl$_3$): 1.3–1.4 (6H, m, CH$_3$CH$_2$O and CH$_3$CH$_2$N); 1.45 (3H, d, J=6 Hz, CH$_3$CH$_2$O); 2.75–2.85 (2H, m, CCH$_2$CH$_2$N); 3.8–3.95 (2H, m, CCH$_2$CH$_2$N); 4.5 (2H, bq, J=6 Hz, CH$_3$CH$_2$N); 4.2 (2H, q, J=6 Hz, CH$_3$CH$_2$O); 4.4 (2H, q, J=6 Hz, CH$_3$CH$_2$O); 4.7–4.8 (2H, bs, CCH$_2$N); 7.25–7.3 (1H, m, aryl-H); 7.9 (1H, d, J=8 Hz, aryl-H); 8.2 (1H, s, aryl-H).

Example 13C

5-Ethyl-8-hydroxymethyl-2-methyl-1,2,5,6-tetrahydropyrido[3,4-b]indole

Ethyl 5-ethyl-2-ethoxycarbonyl-1,2,3,4-tetrahydropyrido[4,3-b]indole-8-carboxylate (0.77 g, 2.25 mmol) was added to a ice-cold solution of lithium aluminum hydride (0.188 g, 4.5 mmol) in anhydrous THF (10 mL) and the reaction was stirred for 4 hours. Sodium hydroxide was then added dropwise (5% solution, 0.61 mL) and the mixture filtered through diatomaceous earth to afford the title compound.

$C_{15}H_{20}N_2O$ Mass (calculated): [244]. (found): [M+H$^+$]= 245. NMR (400 MHz, CDCl$_3$): 1.3 (3H, d, J=6 Hz, CH$_3$CH$_2$N); 2.5 (3H, s, NCH$_3$); 2.8 (4H, bs, CCH$_2$CH$_2$N); 3.5 (2H, bs, CCH$_2$N); 4.0 (2H, q, J=6 Hz, CH$_3$CH$_2$N); 4.65 (2H, s, CH$_2$OH); 7.1 (1H, d, J=8 Hz, aryl-H); 7.2 (1H, d, J=8 Hz, aryl-H); 7.25 (1H, s, aryl-H).

Example 13D

5-Ethyl-2-methyl-1,2,5,6-tetrahydropyrido[3,4-b]indole-8-carboxaldehyde

A solution of 5-Ethyl-8-hydroxymethyl-2-methyl-1,2,3,4-tetrahydropyrido[4,3-b]indole (0.73 g, 2.98 mmol) in acetone (40 mL) was treated with MnO$_2$ (3.66 g) and stirred at room temperature for 72 hours. The solid was filtered and the solvent removed in vacuo to afford 0.67 g of title compound.

$C_{15}H_{18}N_2O$ Mass (calculated): [242]. (found): [M+H$^+$]= 243. NMR (400 MHz, CDCl$_3$): 1.3 (3H, d, J=6 Hz, CH$_3$CH$_2$N); 2.55 (3H, s, NCH$_3$); 2.8 (4H, bs, CCH$_2$CH$_2$N); 3.65 (2H, bs, CCH$_2$N); 4.05 (2H, q, J=6 Hz, CH$_3$CH$_2$N); 7.3 (1H, d, J=8 Hz, aryl-H); 7.7 (1H, dd, J=1 and 8 Hz, aryl-H); 7.9 (1H, d, J=1, aryl-H).

Example 13E (R)-N-(1-((Phenyl)ethyl)-N-((5-ethyl-2-methyl-1,2,5,6-tetrahydropyrido[3,4-b]indole-8-yl)methyl)amine Prepared according to general procedure C.

$C_{23}H_{29}N_3$ Mass (calculated): [347]. (found): [M+H$^+$]= 348. NMR (400 MHz, CDCl$_3$): 1.25 (3H, t, J=6 Hz, CH$_3$CH$_2$N); 1.3 (3H, d, J=6 Hz, CH$_3$CHN); 2.5 (3H, s, NCH$_3$); 2.85 (4H, bs, CCH$_2$CH$_2$N); 3.55–3.65 (3H, m, CCH$_2$N and aryl-CH$_2$N); 3.7 (1H, d, J=12 Hz, aryl-CH$_2$N); 4.0 (2H, q, J=6 Hz, CH$_3$CH$_2$N);); 7.0 (1H, dd, J=1 and 8 Hz, aryl-H); 7.15–7.25 (3H, m, aryl-H); 7.3–7.4 (4H, m, aryl-H).

EXAMPLE 14

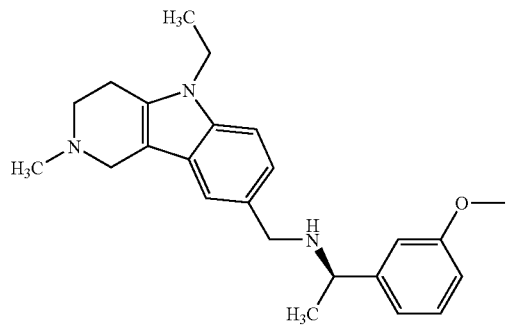

(R)-N-(1-((3-Methoxyphenyl)ethyl)-N-((5-ethyl-2-methyl-1,2,5,6-tetrahydropyrido[3,4-b]indole-8-yl)methyl)amine Prepared according to general procedure C.

$C_{24}H_{31}N_3O$ Mass (calculated): [377]. (found): [M+H$^+$]= 227, 378. NMR (400 MHz, CDCl$_3$): 1.25 (3H, t, J=6 Hz, CH$_3$CH$_2$N); 1.3 (3H, d, J=6 Hz, CH$_3$CHN); 2.5 (3H, s, NCH$_3$); 2.8 (4H, bs, CCH$_2$CH$_2$N); 3.55–3.8 (8H, m, CCH$_2$N, aryl-CH$_2$N, CH$_3$CH$_2$N and OCH$_3$); 4.0 (2H, q, J=6 Hz, CH$_3$CH$_2$N);); 6.7–6.8 (1H, m, aryl-H); 6.85–6.9 (1H, m, aryl-H); 7.0 (1H, dd, J=1 and 8 Hz, aryl-H); 7.1–7.3 (4H, m, aryl-H).

EXAMPLE 15

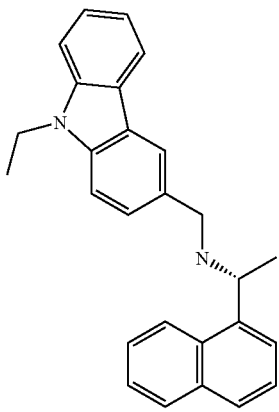

(R)-N-(1-(1-Naphthyl)ethyl)-N-(9-ethyl-3-carbazolylmethyl)amine

Prepared according to general procedure C.

$C_{27}H_{26}N_2O$ Mass (calculated): [378].(found): [M+H$^+$]= 379. NMR (400 MHz, CDCl$_3$): 1.5 (3H, t, J=7 Hz, CH$_3$CH$_2$); 1.65 (3H, d, J=7 Hz, NCHCH$_3$); 3.9 and 4.0 (2H, dd, J=14 Hz, CH$_2$N); 4.4 (2H, q, J=7 Hz, CH$_3$CH$_2$); 4.85 (1H, q, J=7 Hz, NCHMe); 7.25 (1H, t, J=7 Hz, aryl-H); 7.35–7.55 (6H, m, aryl-H); 7.6 (1H, t, J=7 Hz, aryl-H); 7.85 (1H, d, J=7 Hz); 7.9–8 (2H, m, aryl-H); 8 (1H, s, aryl-H); 8.05 (1H, d, J=7 Hz, aryl-H); 8.2 (1H, bd, J=7 Hz; aryl-H).

EXAMPLE 16

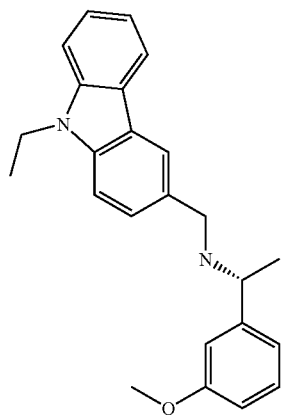

(R)-N-(1-(3-Methoxyphenyl)ethyl)-N-(9-ethyl-3-carbazolylmethyl)amine

Prepared according to general procedure C.

$C_{24}H_{26}N_2O$ Mass (calculated): [358]. (found): [M+H$^+$]= 359. NMR (400 MHz, CDCl$_3$): 1.3–1.4 (6H, m, NCHCH$_3$ and CH$_2$CH$_3$); 3.7 (1H, d, J=12 Hz, CH$_2$N); 3.75–3.83 (5H, m, CH$_2$N, CHCH$_3$, OCH$_3$); 4.3 (2H, q, J=7 Hz, CH$_2$CH$_3$); 6.75 (1H, m, aryl-H); 6.9 (2H, m, aryl-H); 7.1–7.42 (6H, m, aryl-H); 7.9 (1H, s, aryl-H); 8.0 (1H, d, J=7 Hz, aryl-H).

EXAMPLE 17

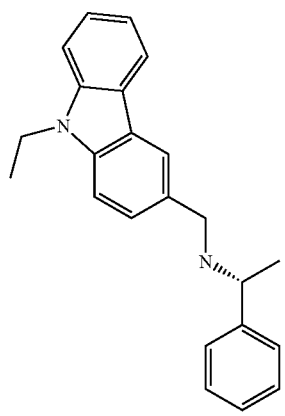

(R)-N-(1-(Phenyl)ethyl)-N-(9-ethyl-3-carbazolylmethyl)amine

Prepared according to general procedure A.

$C_{24}H_{26}N_2O$ Mass (calculated): [328]. (found): [M+H$^+$]= 208, 329. NMR (400 MHz, CDCl$_3$): 1.3–1.4 (6H, m, NCHCH$_3$ and CH$_2$CH$_3$); 3.7 (1H, d, J=12 Hz, CH$_2$N); 3.75–3.83 (5H, m, CH$_2$N, CHCH$_3$, OCH$_3$); 4.3 (2H, q, J=7 Hz, CH$_2$CH$_3$); 6.75 (1H, m, aryl-H); 6.9 (2H, m, aryl-H); 7.1–7.42 (6H, m, aryl-H); 7.9 (1H, s, aryl-H); 8.0 (1H, d, J=7 Hz, aryl-H).

EXAMPLE 18

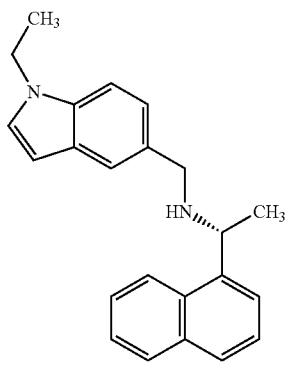

(R)-N-(1-(1-Naphthyl)ethyl)-N-((1-ethylindole-5-yl)methyl)amine

Prepared according to general procedure C.

$C_{23}H_{24}N_2$ Mass (calculated): [328]. (found): [M+H$^+$]= 329, 157. NMR (400 MHz, CDCl$_3$): 1.29 (3H, t, J=7.6 Hz, CH$_2$CH$_3$); 1.39 (3H, d, J=6.6 Hz; CHCH$_3$); 3.67 and 3.76 (2H, dd, J=12.7 Hz, CH$_2$N); 4.0 (2H, q, J=7.6 Hz, CH$_2$CH$_3$); 4.6 (1H, q, J=6.6 Hz, CHCH$_3$); 6.32 (1H, d, J=3 Hz, indole-H); 6.95 (1H, d, J=3 Hz, indole-H); 7.05 (1H, dd, J=1.5 and 8 Hz, aryl-H); 7.16 (1H, d, J=8.6 Hz, aryl-H); 7.3–7.5 (3H, m, aryl-H); 7.63 (1H, d, J=7.6 Hz, aryl-H); 7.7–7.8 (2H, m, aryl-H); 8.0–8.1 (1H, m, aryl-H).

EXAMPLE 19

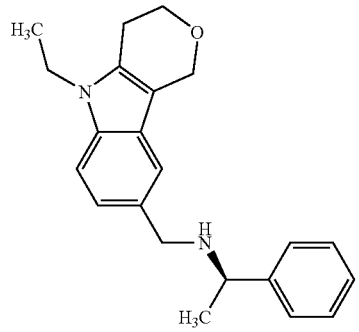

(R)-N-(1-((Phenyl)ethyl)-N-((5-ethyl-5,6-dihydro-2H-pyrano[3,4-b]indole-8-yl)methyl)amine

Example 19A

Methyl 1,2,5,6-tetrahydropyrido[3,4-b]indole-8-carboxylate

Tetrahydro-4H-pyran-4-one (1.3 g, 13 mmol), 4-amino-3-iodobenzoic acid methyl ester (3.46 g, 12.5 mmol), DABCO (4.37 g, 39 mmol), MgSO$_4$ (2.35 g, 19.5 mmol) and Pd(OAc)$_2$ (0.15 g, 0.00065 mol) were dissolved in DMF (18 mL) and heated under nitrogen at 105° C. for 2 days. The reaction mixture was then partitioned between ethyl acetate and water, and extracted. The crude was purified by column chromatography (98/2 DCM/MeOH) to give 0.62 g of title compound.

$C_{13}H_{13}NO_3$ Mass (calculated): [231]. (found): [M+H$^+$]= 232. NMR (400 MHz, acetone-d$_6$): 2.7–2.8 (2H, m, CCH$_2$CH$_2$O); 3.8 (3H, s, CH$_3$O); 3.8–3.85 (2H, m, CCH$_2$CH$_2$O); 4.75–4.8 (2H, m, CCH$_2$O); 7.3 (1H, d, J=8 Hz, aryl-H); 7.65 (1H, dd, J=1 and 8 Hz); 8 (1H, d, J=1 Hz, aryl-H).

Example 19B

Methyl 5-ethyl-1,2,5,6-tetrahydropyrido[3,4-b]indole-8-carboxylate

Ethyl 1,2,5,6-tetrahydropyrido[3,4-b]indole-8-carboxylate (0.62 g, 2.68 mmol) was dissolved in DMF (10 mL) and cooled to 0° C. Sodium hydride (60% suspension in mineral oil, 0.16 g, 6.7 mmol) was added and the mixture stirred for 45 min prior to addition of ethyl iodide (0.50 g, 3.22 mmol). The mixture was stirred for 15 hours, then quenched with water and extracted with ethyl acetate. The organic layer was then removed and the crude was redissolved in acetonitrile and then washed with hexane to remove the mineral oil. The acetonitrile layer was evaporated to afford 0.5 g of title compound.

$C_{15}H_{17}NO_3$ Mass (calculated): [259]. (found): [M+H$^+$]= 260. NMR (400 MHz, CDCl$_3$): 1.25 (3H, t, J=6 Hz, CH$_3$CH$_2$N); 2.7–2.8 (2H, m, CCH$_2$CH$_2$O); 3.8 (3H, s, CH$_3$O); 3.9–4.0 (4H, m, CCH$_2$CH$_2$O and CH$_3$CH$_2$N); 4.9–4.95 (2H, m, CCH$_2$O); 7.3 (1H, d, J=8 Hz, aryl-H); 7.75 (1H, dd, J=1 and 8 Hz); 8 (1H, d, J=1 Hz, aryl-H).

Example 19C

5-Ethyl-8-hydroxymethyl-1,2,5,6-tetrahydropyrido[3,4-b]indole

Ethyl 1,2,5,6-tetrahydropyrido[3,4-b]indole-8-carboxylate (0.56 g, 2.16 mmol) was dissolved in dry THF (30 mL) and lithium aluminum hydride (1M in THF, 10.82 mL, 10.82 mmol) was added via syringe. The mixture was heated to reflux for one hour then cooled and NaOH (5% aqueous solution, 2.67 mL) was added. The mixture was filtered through diatomaceous earth and the solvent was removed to afford 0.5 g of title compound.

$C_{14}H_{17}NO_2$ Mass (calculated): [231]. (found): [M+H$^+$]= 232. NMR (400 MHz, CDCl$_3$): 1.25 (3H, t, J=6 Hz, CH$_3$CH$_2$N); 2.7–2.8 (2H, m, CCH$_2$CH$_2$O); 3.9–4.0 (4H, m, CCH$_2$CH$_2$O and CH$_3$CH$_2$N); 4.65 (2H, S, CH$_2$OH); 4.8–4.85 (2H, m, CCH$_2$O); 7.1 (1H, d, J=8 Hz, aryl-H); 7.35 (1H, d, J=8 Hz); 7.4 (1H, s, aryl-H).

Example 19D

5-Ethyl-1,2,5,6-tetrahydropyrido[3,4-b]indole-8-carboxyaldehyde 5-ethyl-8-hydroxymethyl-1,2,5,6-tetrahydropyrido[3,4-b]indole (0.5 g, 2.16 mmol) was dissolved in acetone (20 mL) and MnO$_2$ (2.6 g) was added. The mixture was stirred for 24 hours then filtered and the filtrate concentrated in vacuo to afford 0.36 g of title compound.

$C_{14}H_{15}NO_2$ Mass (calculated): [229]. (found): [M+H$^+$]= 230. NMR (400 MHz, CDCl$_3$): 1.25 (3H, t, J=6 Hz, CH$_3$CH$_2$N); 2.7–2.8 (2H, m, CCH$_2$CH$_2$O); 4.0–4.1 (4H, m, CCH$_2$CH$_2$O and CH$_3$CH$_2$N); 4.9–4.95 (2H, m, CCH$_2$O); 7.3 (1H, d, J=8 Hz, aryl-H); 7.7 (1H, d, J=8 Hz); 7.9 (1H, s, aryl-H); 10 (1H, s, CHO)

Example 19E (R)-N-(1-((Phenyl)ethyl)-N-((5-ethyl-5,6-dihydro-2H-pyrano[3,4-b]indol-8-yl)methyl)amine Prepared according to general procedure C.
$C_{22}H_{26}N_2O$ Mass (calculated): [334]. (found): [M+H$^+$]= 335. NMR (400 MHz, CDCl$_3$): 1.25 (3H, t, J=6 Hz, CH$_3$CH$_2$N); 1.3 (3H, d, J=6 Hz, CH$_3$CHN); 2.7–2.8 (2H, m, CCH$_2$CH$_2$O); 3.6 and 3.7 (2H, dd, J=12 Hz, aryl-CH$_2$N); 3.8 (1H, q, J=6 Hz, CH$_3$CHN); 3.9–4.05 (4H, m, CH$_2$CH$_2$O and CH$_3$CH$_2$N); 4.85–4.9 (2H, m, CCH$_2$O); 7.05 (1H, dd, J=1 and 8 Hz, aryl-H); 7.15–7.25 (3H, m, aryl-H); 7.3–7.4 (4H, m, aryl-H).

EXAMPLE 20

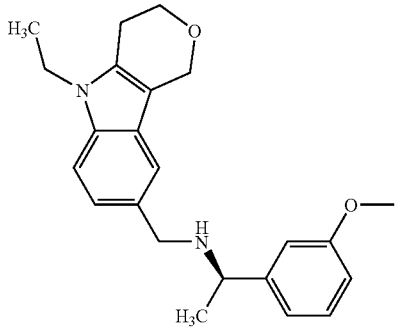

(R)-N-(1-((3-Methoxyphenyl)ethyl)-N-((5-ethyl-5,6-dihydro-2H-pyrano[3,4-b]indol-8-yl)methyl)amine Prepared according to general procedure C.
$C_{23}H_{28}N_2O_2$ Mass (calculated): [364]. (found): [M+H$^+$]= 365. NMR (400 MHz, CDCl$_3$): 1.25 (3H, t, J=6 Hz, CH$_3$CH$_2$N); 1.3 (3H, d, J=6 Hz, CH$_3$CHN); 2.7–2.8 (2H, m, CCH$_2$CH$_2$O); 3.6 and 3.7 (2H, dd, J=12 Hz, aryl-CH$_2$N); 3.8–3.9 (4H, m, CH$_3$O and CH$_3$CHN); 3.9–4.05 (4H, m, CH$_2$CH$_2$O and CH$_3$CH$_2$N); 4.85–4.9 (2H, m, CCH$_2$O); 6.75 (1H, dd, J=1 and 8 Hz, aryl-H); 7.05 (1H, dd, J=2 and 8 Hz, aryl-H); 6.8–6.9 (2H, m, aryl-H); 7.05 (1H, dd, J=1 and 8 Hz, aryl-H); 7.2–7.4 (3H, m, aryl-H).

EXAMPLE 21

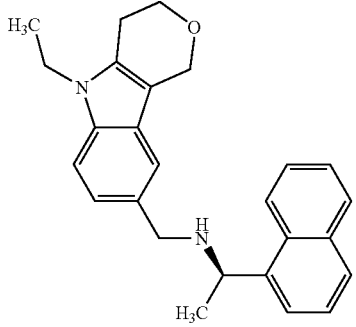

(R)-N-(1-((1-naphthyl)ethyl)-N-((5-ethyl-5,6-dihydro-2H-pyrano[4,3-b]indol-8-yl)methyl)amine Prepared according to general procedure C.
$C_{22}H_{28}N_2O$ Mass (calculated): [384]. (found): [M+H$^+$]= 385. NMR (400 MHz, CDCl$_3$): 1.25 (3H, t, J=6 Hz, CH$_3$CH$_2$N); 1.45 (3H, d, J=6 Hz, CH$_3$CHN); 2.7–2.8 (2H, m, CCH$_2$CH$_2$O); 3.7 and 3.8 (2H, dd, J=12 Hz, aryl-CH$_2$N); 3.9–4.05 (4H, m, CH$_2$CH$_2$O and CH$_3$CH$_2$N); 4.8 (1H, q, J=6 Hz, CH$_3$CHN); 4.85–4.9 (2H, m, CCH$_2$O); 7.0–7.2 (3H, m, aryl-H); 7.35–7.55 (3H, m, aryl-H); 7.7 (1H, d, J=8 Hz, aryl-H); 7.8–7.85 (2H, m, aryl-H); 7.9–8 (1H, m, aryl-H)

EXAMPLE 22

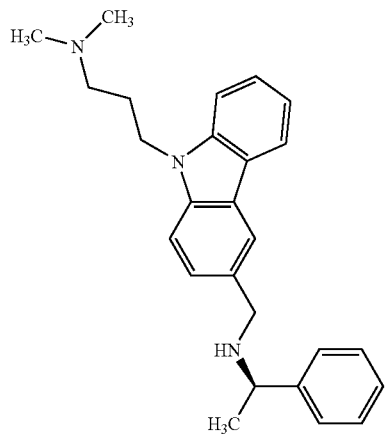

(R)-N-(1-(Phenyl)ethyl)-N-(9-(3-(N,N-dimethylamino)propyl)-3-carbazolylmethyl)amine

Example 22A 9-(3-chloropropyl)carbazole

Prepared as in WO9634863.
$C_{15}H_{14}ClN$ Mass (calculated): [243]. 2.3 (2H, quintet, J=6 Hz, ClCH$_2$CH$_2$CH$_2$N); 3.4 (2H, t, J=6 Hz, ClCH$_2$CH$_2$CH$_2$N); 4.45 (2H, t, J=6 Hz, ClCH$_2$CH$_2$CH$_2$N); 7.15–7.25 (2H, m, aryl-H); 7.35–7.45 (4H, m, aryl-H); 8.0–8.1 (2H, m, aryl-H).

Example 22B 9-(3-(N,N-dimethylamino)propyl)carbazole 9-(3-chloropropyl)carbazole (2.5 g, 10 mmol) was dissolved in acetonitrile (50 mL) in a pressure tube and dimethylamine hydrochloride (12.2 g, 150 mmol, followed by K$_2$CO$_3$ (20.8 g, 150 mmol) and potassium iodide (0.2 g, 1 mmol) were added and the mixture was stirred at room temperature for 7 days, then filtered and the filtrate concentrated in vacuo. The crude was purified by column chromatography (eluting with 5% methanol in dichloromethane) to afford 1.87 g of the title compound.
$C_{17}H_{20}N_2$ Mass (calculated): [252]. (found): [M+H$^+$]= 253.

Example 22C 9-(3-(N,N-Dimethylamino)propyl)carbazole-3-carboxyaldehyde

A solution of 9-(3-(N,N-dimethylamino)propyl)carbazole (0.37 g, 1.45 mmol) was dissolved in dichloromethane (6 mL) and the solution cooled to 0° C. Aluminum trichloride (0.39 g, 2.91 mmol) was then added and the mixture was stirred for 10 minutes. A solution of dichloromethyl methyl ether (0.17 g, 1.45 mmol) in dichloromethane (3 mL) was then added dropwise to the ice-cold mixture and reaction stirred at 0° C. for 4 hours. Water (10 mL) was then added and the pH adjusted to 9 by addition of potassium carbonate. The mixture was stirred for 16 hours then extracted with dichloromethane. The organic layer was dried over sodium sulfate to afford 0.3 g of the title compound.

Mass (calculated): [280]. (found): [M+H$^+$]=281. 1.95 (2H, quintet, J=6 Hz, NCH$_2$CH$_2$CH$_2$N); 2.15 (6H, s, (CH$_3$)$_2$N); 2.2 (2H, t, J=6 Hz, NCH$_2$CH$_2$CH$_2$N); 4.35 (2H, t, J=6 Hz, NCH$_2$CH$_2$CH$_2$N); 7.25–7.3 (1H, m, aryl-H); 7.45–7.55 (3H, m, aryl-H); 7.95 (1H, dd, J=1 and 8 Hz, aryl-H); 8.1 (1H, d, J=8 Hz, aryl-H); 8.55 (1H, d, J=1 Hz, aryl-H); 10.0 (1H, s, CHO).

Example 22D (R)-N-(1-(Phenyl)ethyl)-N-(9-(3-(N,N-dimethylamino)propyl)-3-carbazolylmethyl)amine Prepared according to general procedure C.

C$_{26}$H$_{31}$N$_3$ Mass (calculated): [385]. (found): [M+H$^+$]=500, 386. NMR (400 MHz, CDCl$_3$): 1.3 (3H, t, J=6 Hz, NCHCH$_3$); 1.95 (2H, quintet, J=6 Hz, NCH$_2$CH$_2$CH$_2$N); 2.15 (6H, s, (CH$_3$)$_2$N); 2.2 (2H, t, J=6 Hz, NCH$_2$CH$_2$CH$_2$N): 3.7 and 3.75 (2H, dd, J=12 Hz, aryl-CH$_2$N); 3.8 (1H, q, J=6 Hz, CHCH$_3$); 4.3 (2H, t, J=6 Hz, NCH$_2$CH$_2$CH$_2$N); 7.1–7.3 (2H, m, aryl-H); 7.4–7.5 (8H, m, aryl-H); 7.9 (1H, s, aryl-H); 8.05 (1H, d, J=8 Hz, aryl-H).

EXAMPLE 23

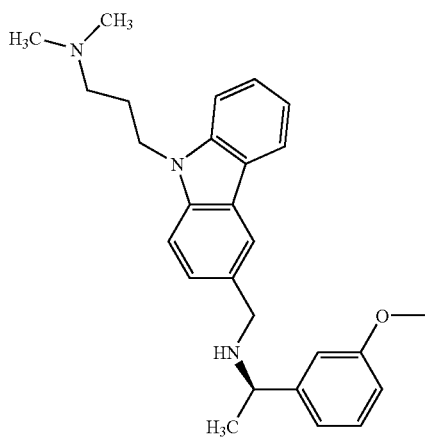

(R)-N-(1-(3-Methoxyphenyl)ethyl)-N-(9-(3-(N,N-dimethylamino)propyl)-3-carbazolylmethyl)amine Prepared according to general procedure C.

C$_{27}$H$_{33}$N$_3$O Mass (calculated): [415]. (found): [M+H$^+$]=530, 416. NMR (400 MHz, CDCl$_3$): 1.3 (3H, t, J=6 Hz, NCHCH$_3$); 1.95 (2H, quintet, J=6 Hz, NCH$_2$CH$_2$CH$_2$N); 2.15 (6H, s, (CH$_3$)$_2$N); 2.2 (2H, t, J=6 Hz, NCH$_2$CH$_2$CH$_2$N): 3.7–3.85 (6H, m, aryl-CH$_2$N, CH$_3$O and CHCH$_3$); 4.3 (2H, t, J=6 Hz, NCH$_2$CH$_2$CH$_2$N); 6.7–6.75 (1H, m, aryl-H); 6.9–6.95 (2H, m, aryl-H); 7.1–7.2 (1H, m, aryl-H); 7.3 (1H, t, J=6 Hz, aryl-H); 7.35–7.4 (2H, m, aryl-H), 7.4 (2H, m, aryl-H); 7.9 (1H, s, aryl-H); 8.05 (1H, d, J=8 Hz, aryl-H).

EXAMPLE 24

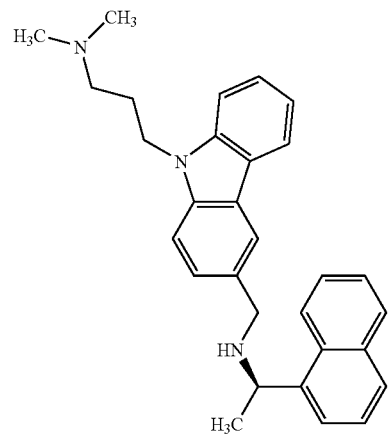

(R)-N-(1-(1-Naphthyl)phenyl)ethyl)-N-(9-(3-(N,N-dimethylamino)propyl)-3-carbazolylmethyl)amine Prepared according to general procedure C.

C$_{30}$H$_{33}$N$_3$ Mass (calculated): [434]. (found): [M+H$^+$]=436, 155, 265. NMR (400 MHz, CDCl$_3$): 1.45 (3H, t, J=6 Hz, NCHCH$_3$); 1.95 (2H, quintet, J=6 Hz, NCH$_2$CH$_2$CH$_2$N); 2.15 (6H, s, (CH$_3$)$_2$N); 2.2 (2H, t, J=6 Hz, NCH$_2$CH$_2$CH$_2$N); 3.75 and 3.85 (2H, dd, J=12 Hz, aryl-CH$_2$N); 4.3 (2H, t, J=6 Hz, NCH$_2$CH$_2$CH$_2$N); 4.7 (1H, q, J=6 Hz, CHCH$_3$); 7.15–7.2 (1H, m, aryl-H); 7.4 (2H, s, aryl-H); 7.45–7.5 (4H, m, aryl-H); 7.55 (1H, t, J=8 Hz, aryl-H); 7.7 (1H, d, J=8 Hz, aryl-H); 7.75 (1H, d, J=8 Hz, aryl-H); 7.9 (1H, s, aryl-H); 7.95) 1H, d, J=8 Hz, aryl-H); 8.1–8.15 (1H, m, aryl-H).

The following compounds were prepared according to General Method C:

EXAMPLE 25

(1R)-N-(1H-indol-5-ylmethyl)-1-(1-naphthalenyl)ethanamine

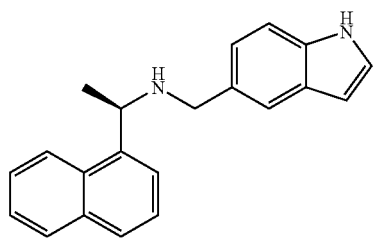

MW 300.41
Mass found: 301

EXAMPLE 26

(1R)-N-((1-ethyl-1H-indol-5-yl)methyl)-1-(1-naphthalenyl)ethanamine

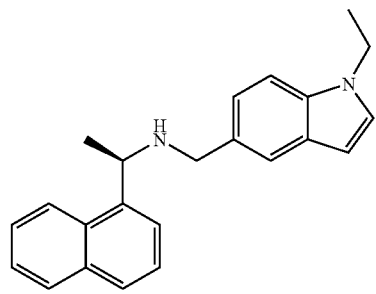

MW 328.457
Mass found: 158, 329

EXAMPLE 27

(1R)-N-((1-ethyl-3-phenyl-1H-indol-5-yl)methyl)-1-(1-naphthalenyl)ethanamine

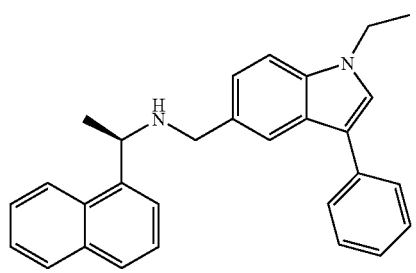

MW 404.554
Mass found: 234, 405

EXAMPLE 28

(1R)-N-((1-ethyl-3-phenyl-1H-indol-5-yl)methyl)-1-phenylethanamine

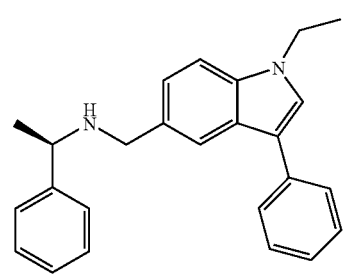

MW 354.494
Mass found: 234, 355, 709

EXAMPLE 29

(1R)-N-((1-ethyl-3-(4-((trifluoromethyl)oxy)phenyl)-1H-indol-5-yl)methyl)-1-phenylethanamine

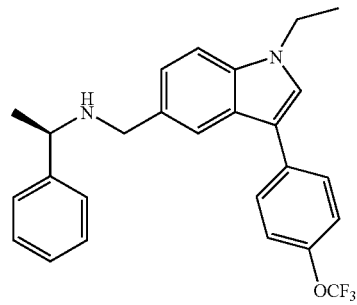

MW 438.491
Mass found: 318, 439

EXAMPLE 30

(1R)-N-((1-ethyl-3-(4-((trifluoromethyl)oxy)phenyl)-1H-indol-5-yl)methyl)-1-(1-naphthalenyl)ethanamine

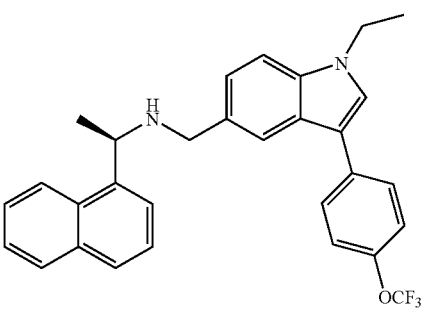

MW 488.55
Mass found: 489, 977

EXAMPLE 31

(1R)-N-((1-ethyl-3-(3-((trifluoromethyl)oxy)phenyl)-1H-indol-5-yl)methyl)-1-phenylethanamine

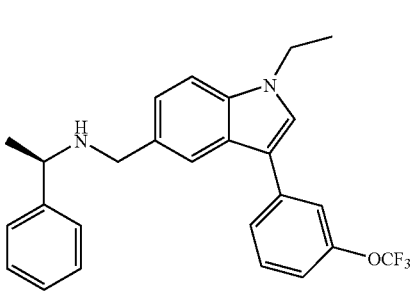

MW 438.491
Mass found: 318, 439

EXAMPLE 32

(1R)-N-((1-ethyl-3-(3-((trifluoromethyl)oxy)phenyl)-1H-indol-5-yl)methyl)-1-(1-naphthalenyl)ethanamine

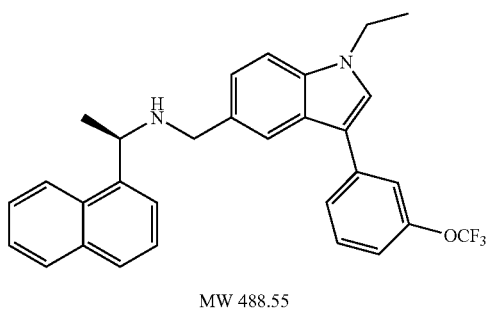

MW 488.55
Mass found: 318, 489

EXAMPLE 33

(1R)-N-((1-ethyl-3-(3-(trifluoromethyl)phenyl)-1H-indol-5-yl)methyl)-1-phenylethanamine

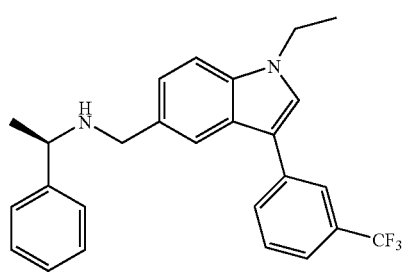

MW 422.491
Mass found: 302

EXAMPLE 34

(1R)-N-((1-ethyl-3-(3-(trifluoromethyl)phenyl)-1H-indol-5-yl)methyl)-1-(1-naphthalenyl)ethanamine

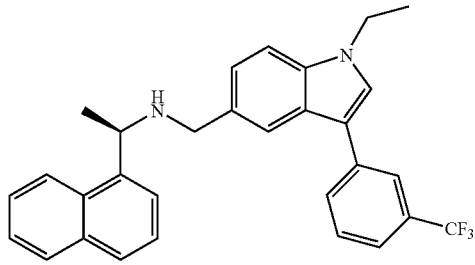

MW 472.551
Mass found: 302, 473

EXAMPLE 35

(1R)-N-((1-ethyl-3-(3-(trifluoromethyl)phenyl)-1H-indol-5-yl)methyl)-1-(3-(methyloxy)phenyl)ethanamine

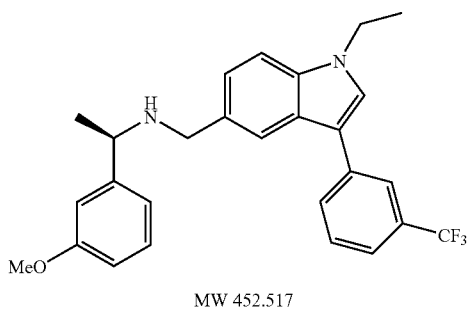

MW 452.517
Mass found: 302

EXAMPLE 36

(1R)-N-((1-ethyl-3-(3-(methyloxy)phenyl)-1H-indol-5-yl)methyl)-1-(3-(methyloxy)phenyl)ethanamine

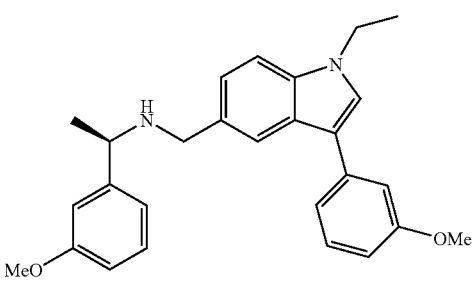

MW 414.546
Mass found: 264

EXAMPLE 37

(1R)-N-((1-ethyl-3-(3-(methyloxy)phenyl)-H-indol-5-yl)methyl)-1-phenylethanamine

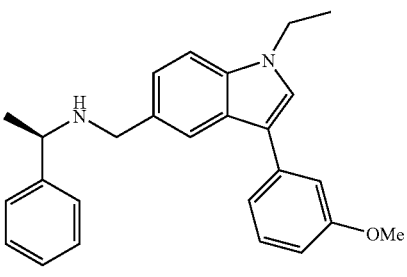

MW 384.52
Mass found: 385, 264, 769

EXAMPLE 38

(1R)-N-((1-ethyl-3-(3-(methyloxy)phenyl)-1H-indol-5-yl)methyl)-1-(1-naphthalenyl)ethanamine

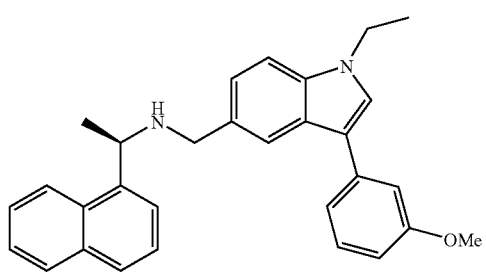

MW 434.58
Mass found: 435, 264

EXAMPLE 39

(1R)-N-((1-ethyl-3-(3-fluorophenyl)-1H-indol-5-yl)methyl)-1-phenylethanamine

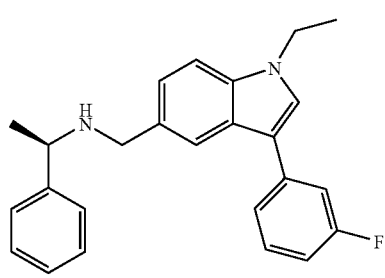

MW 372.484
Mass found: 252, 373, 745

EXAMPLE 40

(1R)-N-((1-ethyl-3-(3-fluorophenyl)-1H-indol-5-yl)methyl)-1-(1-naphthalenyl)ethanamine

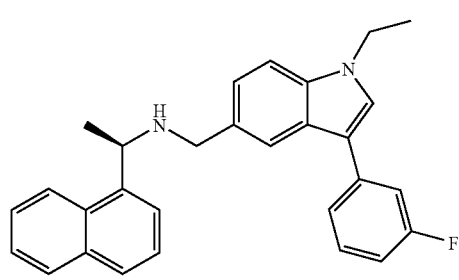

MW 422.544
Mass found: 423, 252

EXAMPLE 41

(1R)-N-((3-(3-chlorophenyl)-1-ethyl-1H-indol-5-yl)methyl)-1-phenylethanamine

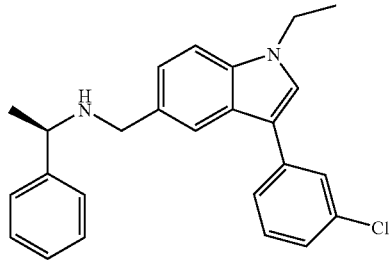

MW 388.94
Mass found: 268, 389, 777

EXAMPLE 42

(1R)-N-((3-(3-chlorophenyl)-1-ethyl-1H-indol-5-yl)methyl)-1-(1-naphthalenyl)ethanamine

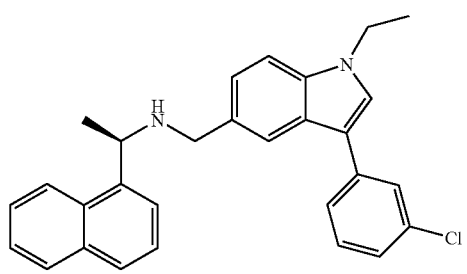

MW 439.00
Mass found: 439, 268

EXAMPLE 43

(1R)-N-((1-ethyl-3-(4-(trifluoromethyl)phenyl)-1H-indol-5-yl)methyl)-1-phenylethanamine

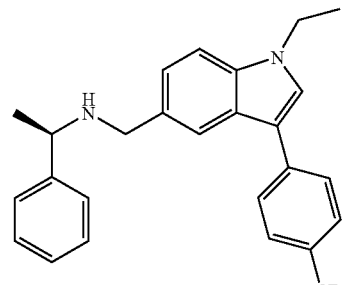

MW 422.491
Mass found: 423, 302

EXAMPLE 44

(1R)-N-((1-ethyl-3-(4-(trifluoromethyl)phenyl)-H-indol-5-yl)methyl)-1-(1-naphthalenyl)ethanamine

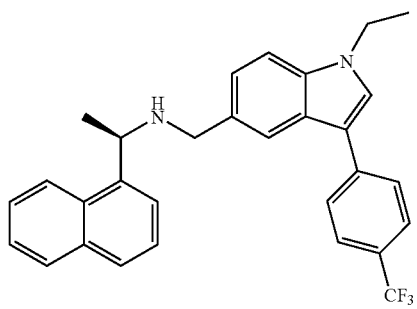

MW 472.551
Mass found: 473, 302

EXAMPLE 45

(1R)-N-((1-ethyl-2-(2-pyridinyl)-1H-indol-5-yl)methyl)-1-(1-naphthalenyl)ethanamine

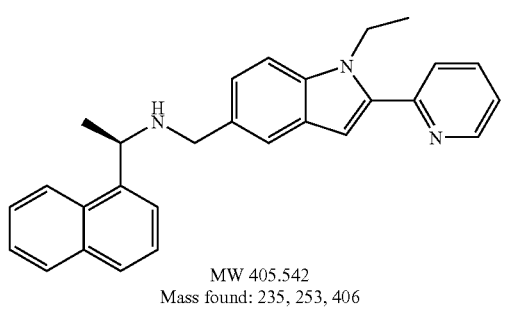

MW 405.542
Mass found: 235, 253, 406

EXAMPLE 46

(1R)-N-((1-ethyl-2-(2-pyridinyl)-1H-indol-5-yl)methyl)-1-(3-(methyloxy)phenyl)ethanamine

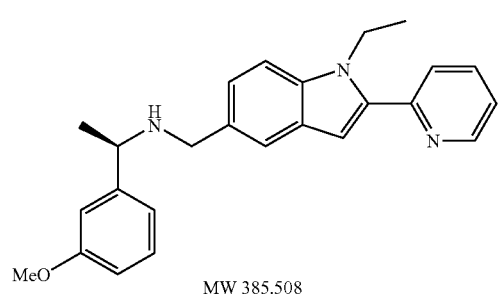

MW 385.508
Mass found: 235, 253, 386

EXAMPLE 47

(1R)-N-((1-ethyl-2-(2-pyridinyl)-1H-indol-5-yl)methyl)-1-phenylethanamine

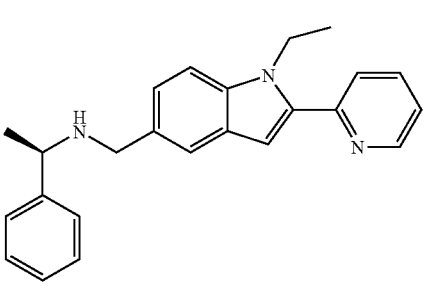

MW 355.483
Mass found: 253, 235, 356

EXAMPLE 48

(1R)-N-((1-ethyl-2-phenyl-1H-indol-5-yl)methyl)-1-phenylethanamine

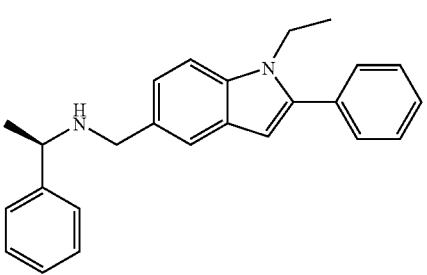

MW 354.494
Mass found: 234, 355

EXAMPLE 49

(1R)-N-((1-ethyl-2-phenyl-1H-indol-5-yl)methyl)-1-(1-naphthalenyl)ethanamine

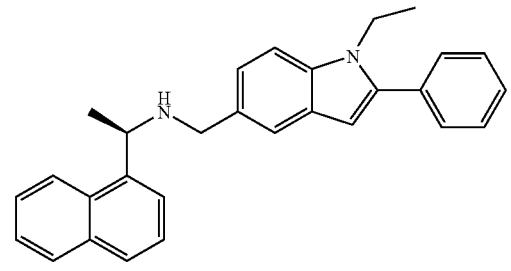

MW 404.5540
Mass found: 234, 405

EXAMPLE 50

(1R)-N-((1-ethyl-2-phenyl-1H-indol-5-yl)methyl)-1-(3-(methyloxy)phenyl)ethanamine

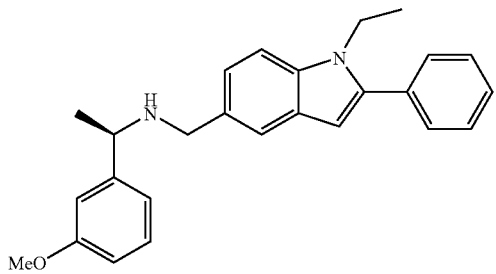

MW 384.52
Mass found: 234, 385

EXAMPLE 51

(1R)-1-phenyl-N-((1-(4-(trifluoromethyl)phenyl)-1H-indol-5-yl)methyl)ethanamine

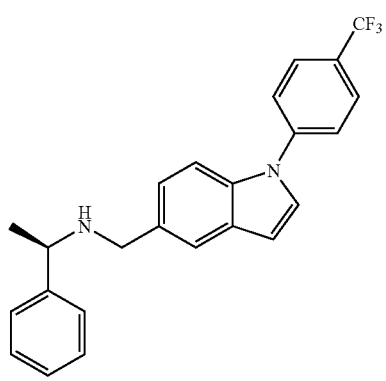

MW 394.438
Mass found: 274, 395

EXAMPLE 52

(1R)-1-(1-naphthalenyl)-N-((1-(4-(trifluoromethyl)phenyl)-1H-indol-5-yl)methyl)ethanamine

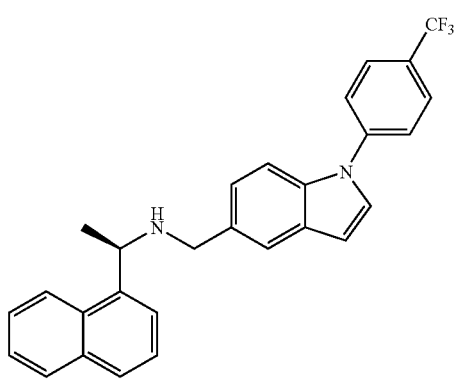

MW 449.498
Mass found: 274, 445

EXAMPLE 53

(1R)-1-(3-(methyloxy)phenyl)-N-((1-(4-(trifluoromethyl)phenyl)-1H-indol-5-yl)methyl)ethanamine

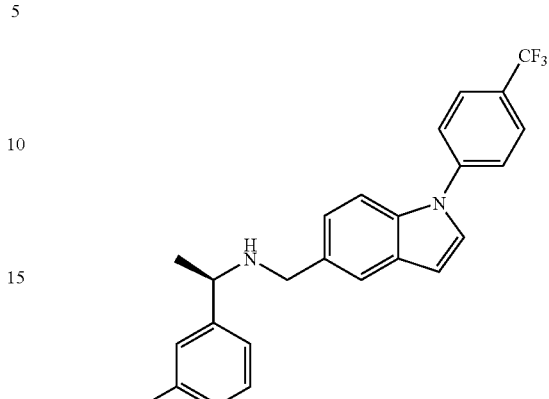

MW 424.464
Mass found: 274, 425

EXAMPLE 54

(1R)-N-((1-ethyl-3-(1,3-oxazol-5-yl)-1H-indol-5-yl)methyl)-1-phenylethanamine

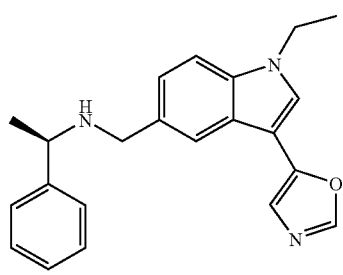

MW 345.444
Mass found: 225, 346, 691

EXAMPLE 55

(1R)-N-((1-ethyl-3-(1-methyl-1H-imidazol-5-yl)-1H-indol-5-yl)methyl)-1-phenylethanamine

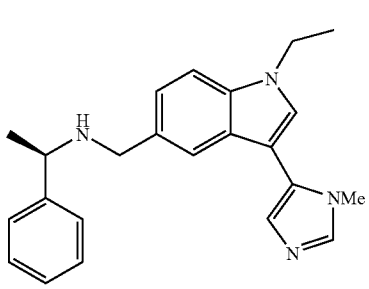

MW 358.486
Mass found: 359, 255

Biological Activity

The activities of the compounds of the present invention on calcium receptors were measured. In one embodiment, the measurement was performed in accordance with the method described in Example 4 of Nemeth et al., PCT/US95/13704 (International Publication No. WO96/12697) herein incorporated by reference.

A 4.0-kb NotI-HindIII fragment of the human parathyroid cell $Ca^{2+}$ receptor (hPCaR) cDNA was subcloned into the mammalian expression vector pCEP4 (Invitrogen) containing the hygromycin-resistant gene as a selectable marker. This plasmid was transfected into HEK 293 cells by calcium phosphate precipitation. Transfected cells were grown in Dulbecco's modified Eagle's medium containing 10% fetal bovine serum and hygromycin (200 μg/mL). Hygromycin-resistant colonies were subcloned and assayed for hPCaR mRNA by solution hybridization using a $^{32}$P-labeled RNA probe complementary to the (4.0 kb) hPCaR sequence (Garrett, et al., J. Biol. Chem. 270, 12919–12925 (1995)). Clone 7 was used to assess the effects of compounds on $[Ca^{2+}]_i$. This stably transfected cell line is termed HEK 293 4.0–7. For measurements of $[Ca^{2+}]_i$, the cells were recovered from tissue culture flasks by brief treatment with 0.02% EDTA and then washed and resuspended in PCB containing 1 mM $CaCl_2$ and 0.1% Bovine Serum Albumin ("BSA"). The cells were loaded with fluo-3 by incubation for 30 min at 37° C., with parathyroid cell buffer (126 mM NaCl, 4 mM KCl, 1 mM $MgSO_4$, 0.7 mM $K_2HPO_4/KH_2PO_4$, 20 mM HEPES.NaOH (pH 7.45)) containing 0.5% BSA in 1 mM $CaCl_2$ and 2 μM fluo-3 acetoxymethyl ester. The cells were subsequently washed, each test compound was added to the cells and the fluorescence was recorded by using excitation and emission wavelengths of 485 and 530 nm, respectively.

The following compounds of the invention were tested acording to the procedure described above and found to have an $EC_{50}$ of 10 μM or less:

(R)-N-(1-(1-Naphthyl)ethyl)-N-(9-ethyl-3-carbazolylmethyl)amine;
(R)-N-(1-(3-Methoxyphenyl)ethyl)-N-(9-ethyl-3-carbazolylmethyl)amine;
(R)-N-(1-(1-Naphthyl)ethyl)-N-(1-ethyl-5-indolylmethyl)amine;
(R)-N-(1-(1-Naphthyl)ethyl)-N-(2'-ethyl-benzotriazol-5-yl-methyl)amine;
(R)-N-(1-(3-Methoxyphenyl)ethyl)-N-(2'-ethyl-benzotriazol-5-ylmethyl)amine;
(R)-N-(1-(Phenyl)ethyl)-N-(2'-ethyl-benzotriazol-5-ylmethyl)amine;
(R)-N-(1-(3-Methoxyphenyl)ethyl)-N-(9-ethyl-6-methoxy-3-carbazolylmethyl)amine;
(R)-N-(1-((Phenyl)ethyl)-N-((1-ethylcyclopent[b]indol-5-yl)methyl)amine;
(R)-N-(1-(1-Naphthyl)ethyl)-N-((1-methylbenzimidazol-5-yl)methyl)amine;
(R)-N-(1-(Phenyl)ethyl)-N-((1-methylbenzimidazol-5-yl)methyl)amine;
(R)-N-(1-((Phenyl)ethyl)-N-((5-ethyl-2-methyl-1,2,5,6-tetrahydropyrido-[3,4-b]indol-8-yl)methyl)amine;
(R)-N-(1-((3-Methoxyphenyl)ethyl)-N-((5-ethyl-2-methyl-1,2,5,6-tetrahydropyrido[3,4-b]indol-8-yl)methyl)amine;
(R)-N-(1-(1-Naphthyl)ethyl)-N-(9-ethyl-3-carbazolylmethyl)amine;
(R)-N-(1-(3-Methoxyphenyl)ethyl)-N-(9-ethyl-3-carbazolylmethyl)amine;
(R)-N-(1-(Phenyl)ethyl)-N-(9-ethyl-3-carbazolylmethyl)amine;
(R)-N-(1-(1-Naphthyl)ethyl)-N-((1-ethylindole-5-yl)methyl)amine;
(R)-N-(1-((Phenyl)ethyl)-N-((5-ethyl-5,6-dihydro-2H-pyrano[3,4-b]indol-8-yl)methyl)amine;
(R)-N-(1-((3-Methoxyphenyl)ethyl)-N-((5-ethyl-5,6-dihydro-2H-pyrano[3,4-b]indol-8-yl)methyl)amine;
(R)-N-(1-((1-naphthyl)ethyl)-N-((5-ethyl-5,6-dihydro-2H-pyrano[4,3-b]indol-8-yl)methyl)amine;
(R)-N-(1-(1-Naphthyl)phenyl)ethyl)-N-(9-(3-(N,N-dimethylamino)propyl)-3-carbazolylmethyl)amine;
(1R)-N-(1H-indol-5-ylmethyl)-1-(1-naphthalenyl)ethanamine;
(1R)-N-((1-ethyl-1H-indol-5-yl)methyl)-1-(1-naphthalenyl)ethanamine;
(1R)-N-((1-ethyl-3-phenyl-1H-indol-5-yl)methyl)-1-phenylethanamine;
(1R)-N-((1-ethyl-3-(4-((trifluoromethyl)oxy)phenyl)-1H-indol-5-yl)methyl)-1-phenylethanamine;

For the treatment of bone disorders, such as osteoporosis, excessive secretion of PTH, such as hyperparathyroidism, and the like, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating the disclosed diseases with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hyroxy-ethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$–$C_4$)alkyloxy)ethyl; for example, methoxyethyl, ethoxyethyl, propoxyethyl, iso-propoxyethyl, etc.; 2-oxo-1,3-dioxolen-4-ylmethyl groups, such as 5-methyl-2-oxo-1,3, dioxolen-4-ylmethyl, etc.; $C_1$–$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula (I):

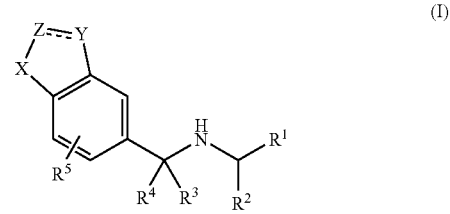

or a pharmaceutically acceptable salt thereof, wherein:

- - - - - represents a double;

$R^1$ is $R^b$;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$ or $NR^dC(=O)R^d$;

$R^6$ is $R^d$, $C_{1-4}$haloalkyl, —C(=O)$R^c$, —$OC_{1-6}$alkyl, —$OR^b$, —$NR^aR^a$, —$NR^aR^b$, —C(=O)$OR^c$, —C(=O)$NR^aR^a$, —OC(=O)$R^c$, —$NR^aC(=O)R^c$, cyano, nitro, —$NR^aS(=O)_mR^c$ or —$S(=O)_mNR^aR^a$;

$R^7$ is $R^d$, $C_{1-4}$haloalkyl, —C(=O)$R^c$, —$OC_{1-6}$alkyl, —$OR^b$, —$NR^aR^a$, —$NR^aR^b$, —C(=O)$OR^c$, —C(=O)$NR^aR^a$, —OC(=O)$R^c$, —$NR^aC(=O)R^c$, cyano, nitro, —$NR^aS(=O)_mR^c$ or —$S(=O)_mNR^aR^a$; or $R^6$ and $R^7$ together form a 3- to 6-atom saturated or unsaturated bridge containing 0, 1, 2 or 3 N atoms and 0, 1 or 2 atoms selected from S and O, wherein the bridge is substituted by 0, 1 or 2 substituents selected from $R^5$; wherein when $R^6$ and $R^7$ form a benzo bridge, then the benzo bridge may be additionally substituted by a 3- or 4-atoms bridge containing 1 or 2 atoms selected from N and O, wherein the bridge is substituted by 0 or 1 substituents selected from $C_{1-4}$alkyl;

$R^a$ is, independently, at each instance, H, $C_{1-4}$haloalkyl or $C_{1-6}$alkyl;

$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —C(=O)$R^c$, —$OR^b$, —$NR^aR^a$, —$NR^aR^b$, —C(=O)$OR^c$, —C(=O)$NR^aR^a$, —OC(=O)$R^c$, —$NR^aC$(=O)$R^c$, —$NR^aS$(=O)$_mR^c$ and —S(=O)$_mNR^aR^a$;

X is —$NR^d$—;

Y is =$CR^6$; and Z is —$CR^7$; and m is 1 or 2.

2. A compound or salt according to claim 1, wherein $R^1$ is naphthyl.

3. A compound or salt according to claim 1, wherein $R^3$ and $R^4$ are H.

4. A compound or salt according to claim 1, wherein $R^5$ is H.

5. A compound or salt according to claim 1, wherein $R^6$ is H.

6. A compound or salt according to claim 1, wherein $R^7$ is H.

7. A compound or salt according to claim 1, having the structure

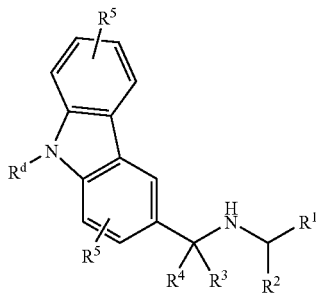

wherein:

$R^1$ is $R^b$;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$ or $NR^dC$(=O)$R^d$;

$R^a$ is, independently, at each instance, H, $C_{1-4}$haloalkyl or $C_{1-6}$alkyl;

$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —C(=O)$R^c$, —$OR^b$, —$NR^aR^a$, —$NR^aR^b$, —C(=O)$OR^c$, —C(=O)$NR^aR^a$, —OC(=O)$R^c$, —$NR^aC$(=O)$R^c$, —$NR^aS$(=O)$_mR^c$ and —S(=O)$_mNR^aR^a$; and m is 1 or 2.

8. A pharmaceutical composition comprising a compound according to claim 1 and a pharmaceutically-acceptable diluent or carrier.

9. A method for the treatment of osteoporosis or hyperparathyroidism in a patient in need therefor comprising administering a compound according to claim 1.

10. The compound according to claim 1 in the manufacture of a medicament for the treatment of osteoporosis or hyperparathyroidism.

(R)-N-(1-(1-Naphthyl)ethyl)-N-(9-ethyl-3-carbazolylmethyl)amine, (R)-N-(1-(3-Methoxyphenyl)ethyl)-N-(9-ethyl-3-carbazolylmethyl)amine, (R)-N-(1-(1-Naphthyl)ethyl)-N-(1-ethyl-5-indolylmethyl)amine, (R)-N-(1-(1-Naphthyl)ethyl)-N-(9-ethyl-6-methoxy-3-carbazolylmethyl)amine, (R)-N-(1-(3-Methoxyphenyl)ethyl)-N-(9-ethyl-6-methoxy-3-carbazolylmethyl)amine, (R)-N-(1-(Phenyl)ethyl)-N-(9-ethyl-6-methoxy-3-carbazolylmethyl)amine, (R)-N-(1-(Phenyl)ethyl)-N-((1-ethylcyclopent[b]indol-5-yl)methyl)amine, (R)-N-(1-(Phenyl)ethyl)-N-((5-ethyl-2-methyl-1,2,5,6-tetrahydropyrido[3,4-b]indol-8-yl)methyl)amine, (R)-N-(1-(3-Methoxyphenyl)ethyl)-N-((5-ethyl-2-methyl-1,2,5,6-tetrahydropyrido[3,4-b]indol-8-yl)methyl)amine, (R)-N-(1-(1-Naphthyl)ethyl)-N-(9-ethyl-3-carbazolylmethyl)amine, (R)-N-(1-(3-Methoxyphenyl)ethyl)-N-(9-ethyl-3-carbazolylmethyl)amine, (R)-N-(1-(Phenyl)ethyl)-N-(9-ethyl-3-carbazolylmethyl)amine, (R)-N-(1-(1-Naphthyl)ethyl)-N-((1-ethylindole-5-methyl)amine, (R)-N-(1-(Phenyl)ethyl)-N-((5-ethyl-5,6-dihydro-2H-pyrano[3,4-b]indol-8-yl)methyl)amine, (R)-N-(1-(3-Methoxyphenyl)ethyl)-N-((5-ethyl-5,6-dihydro-2H-pyrano[3,4-b]indol-8-yl)methyl)amine, (R)-N-(1-(1-naphthyl)ethyl)-N-((5-ethyl-5,6-dihydro-2H-pyrano[4,3-b]indol-8-yl)methyl)amine, (R)-N-(1-(Phenyl)ethyl)-N-(9-(3-(N,N-dimethylamino)propyl)-3-carbazolylmethyl)amine, (R)-N-(1-(3-Methoxyphenyl)ethyl)-N-(9-(3-(N,N-dimethylamino)propyl)-3-carbazolylmethyl)amine, (R)-N-(1-(1-Naphthyl)phenyl)ethyl)-N-(9-(3-(N,N-dimethylamino)propyl)-3-carbazolylmethyl)amine, (1R)-N-(1H-indol-5-ylmethyl)-1-(1-naphthalenyl)ethanamine, (1R)-N-((1-ethyl-1H-indol-5-yl)methyl)-1-(1-naphthalenyl)ethanamine, (1R)-N-((1-ethyl-3-phenyl-1H-indol-5-yl)methyl)-1-(1-naphthalenyl)ethanamine, (1R)-N-((1-ethyl-3-phenyl-1H-indol-5-yl)methyl)-1-phenylethanamine, (1R)-N-((1-ethyl-3-(4-(((trifluoromethyl)oxy)phenyl)-1H-indol-5-yl)methyl)-1-phenylethanamine,
(1R)-N-((1-ethyl-3-(4-(((trifluoromethyl)oxy)phenyl)-1H-indol-5-yl)methyl)-1-(1-naphthalenyl)ethanamine,
(1R)-N-((1-ethyl-3-(3-(((trifluoromethyl)oxy)phenyl)-1H-indol-5-yl)methyl)-1-phenylethanamine,
(1R)-N-((1-ethyl-3-(3-(((trifluoromethyl)oxy)phenyl)-1H-indol-5-yl)methyl)-1-(1-naphthalenyl)ethanamine,
(1R)-N-((1-ethyl-3-(3-(trifluoromethyl)phenyl)-1H-indol-5-yl)methyl)-1-pheny)ethanamine,
(1R)-N-((1-ethyl-3-(3-(trifluoromethyl)phenyl)-1H-indol-5-yl)methyl)-1-(1-naphthalcnyl)ethanamine,
(1R)-N-((1-ethyl-3-(3-(trifluoromethyl)phenyl)-1H-indol-5-yl)methyl)-1-(3-(methyloxy)phenyl)ethanamine,
(1R)-N-((1-ethyl-3-(3-(methyloxy)phenyl)-1H-indol-5-yl)methyl)-1-(3-(methyloxy)phenyl)ethanamine,
(1R)-N-((1-ethyl-3-(3-(methyloxy)phenyl)-1H-indol-5-yl)methyl)-1-phenylethanamine,
(1R)-N-((1-ethyl-3-(3-(methyloxy)phenyl)-1H-indol-5-yl)methyl)-1-(1-naphthalenyl)ethanamine,
(1R)-N-((1-ethyl-3-(3-fluorophenyl)-1H-indol-5-yl)methyl)-1-phenylethanamine,
(1R)-N-((1-ethyl-3-(3-fluorophenyl)-1H-indol-5-yl)methyl)-1-(1-naphthalenyl)ethanamine,
(1R)-N-((3-(3-chlorophenyl)-1-ethyl-1H-indol-5-yl)methyl)-1-phenylethanamine,
(1R)-N-((3-(3-chlorophenyl)-1-ethyl-1H-indol-5-yl)methyl)-1-(1-naphthalenyl)ethanamine,
(1R)-N-((1-ethyl-3-(4-(trifluoromethyl)phenyl)-1H-indol-5-yl)methyl)-1-phenylethanamine,
(1R)-N-((1-ethyl-3-(4-(trifluoromethyl)phenyl)-1H-indol-5-yl)methyl)-1-(1-naphthalenyl)ethanamine,
(1R)-N-((1-ethyl-2-(2-pyridinyl)-1H-indol-5-yl)methyl)-1-(1-naphthalenyl)ethanamine,
(1R)-N-((1-ethyl-2-(2-pyridinyl)-1H-indol-5-yl)methyl)-1-(3-(methyloxy)phenyl)ethanamine,
(1R)-N-((1-ethyl-2-(2-pyridinyl)-1H-indol-5-yl)methyl)-1-phenylethanamine,
(1R)-N-((1-ethyl-2-phenyl-1H-indol-5-yl)methyl)-1-phenylethanamine,
(1R)-N-((1-ethyl-2-phenyl-1H-indol-5-yl)methyl)-1-(1-naphthalenyl)ethanamine,
(1R)-N-((1-ethyl-2-phenyl-1H-indol-5-yl)methyl)-1-(3-(methyloxy)phenyl)ethanamine,
(1R)-1-phenyl-N-((1-(4-(trifluoromethyl)phenyl)-1H-indol-5-yl)methyl)ethanamine,
(1R)-1-(1-naphthalenyl)-N-((1-(4-(trifluoromethyl)phenyl)-1H-indol-5-yl)methyl)ethanamine,
(1R)-1-(3-(methyloxy)phenyl)-N-((1-(4-(trifluoromethyl)phenyl)-1H-indol-5-yl)methyl)ethanamine,
(1R)-N-((1-ethyl-3-(1,3-oxazol-5-yl)-1H-indol-5-yl)methyl)-1-phenylethanamine, and
(1R)-N-((1-ethyl-3-(1-methyl-1H-imidazol-5-yl-1H-indol-5-yl)methyl)-1-phenylethanamine.

11. A phannaccutical composition comprising a compound according to claim 10 and a pharmaceutically acceptable diluent or carrier.

12. A method for the treatment of osteoporosis or hyperparathyroidism in a patient in need thereof comprising administering a pharmaceutical composition according to claim 8.

* * * * *